US009754082B2

(12) United States Patent
Taylor et al.

(10) Patent No.: US 9,754,082 B2
(45) Date of Patent: Sep. 5, 2017

(54) SYSTEMS AND METHODS FOR REPORTING BLOOD FLOW CHARACTERISTICS

(71) Applicant: HeartFlow, Inc., Redwood City, CA (US)

(72) Inventors: Charles A. Taylor, San Mateo, CA (US); Gregory R. Hart, Palo Alto, CA (US)

(73) Assignee: HeartFlow, Inc., Redwood City, CA (US)

( * ) Notice: Subject to any disclaimer, the term of this patent is extended or adjusted under 35 U.S.C. 154(b) by 0 days.

(21) Appl. No.: 14/480,870

(22) Filed: Sep. 9, 2014

(65) Prior Publication Data

US 2015/0342537 A1 Dec. 3, 2015

Related U.S. Application Data

(60) Provisional application No. 62/005,272, filed on May 30, 2014.

(51) Int. Cl.
A61B 5/02 (2006.01)
G06F 19/00 (2011.01)
A61B 5/026 (2006.01)
A61B 5/00 (2006.01)

(52) U.S. Cl.
CPC .......... G06F 19/3437 (2013.01); A61B 5/026 (2013.01); A61B 5/02007 (2013.01); A61B 5/743 (2013.01); A61B 5/7475 (2013.01); G06F 19/321 (2013.01); G06F 19/322 (2013.01)

(58) Field of Classification Search
CPC ... A61B 5/7275; A61B 5/02007; A61B 5/743; A61B 5/026; A61B 2576/00

USPC .......... 600/504, 416, 419, 410, 411
See application file for complete search history.

(56) References Cited

U.S. PATENT DOCUMENTS 6,616,611 B1 * 9/2003 Moehring .................... 600/454
8,315,812 B2 11/2012 Taylor
8,548,778 B1 10/2013 Hart
8,824,752 B1 9/2014 Fonte et al.
(Continued)

OTHER PUBLICATIONS

International Search Report and Written Opinion mailed on Sep. 30, 2015, in corresponding International PCT Application No. PCT/US15/33030, filed on May 30, 2015 (10 pages).
(Continued)

Primary Examiner — Tiffany Weston
Assistant Examiner — Tho Tran
(74) Attorney, Agent, or Firm — Bookoff McAndrews, PLLC

(57) ABSTRACT

Embodiments include a system for displays cardiovascular information for a patient. The system may include at least one computer system configured to receive patient-specific data regarding a geometry of the patient's heart and create a model representing at least a portion of the patient's heart based on the patient-specific data. The computer system may determine at least one value of the blood flow characteristic within the patient's heart based on the model. The computer system may also display a report comprising a representation of at least one artery corresponding to at least a portion the model, and display one or more indicators of the value of the blood flow characteristic on a corresponding portion of the at least one artery.

18 Claims, 34 Drawing Sheets

(56) References Cited

U.S. PATENT DOCUMENTS

| | | | |
|---|---|---|---|
| 2002/0045830 A1* | 4/2002 | Powers | A61B 8/06 600/459 |
| 2004/0243006 A1 | 12/2004 | Nakata et al. | |
| 2005/0203427 A1* | 9/2005 | Judy | 600/506 |
| 2007/0238999 A1 | 10/2007 | Specht | |
| 2008/0118131 A1 | 5/2008 | Skinner et al. | |
| 2009/0043208 A1 | 2/2009 | Hergum et al. | |
| 2010/0086189 A1 | 4/2010 | Wang et al. | |
| 2010/0130866 A1* | 5/2010 | Main et al. | 600/455 |
| 2010/0157041 A1* | 6/2010 | Klaiman et al. | 348/77 |
| 2011/0066042 A1* | 3/2011 | Pandia et al. | 600/484 |
| 2011/0074813 A1* | 3/2011 | Masumoto | G06T 19/00 345/629 |
| 2011/0319762 A1* | 12/2011 | Lerman | A61B 8/06 600/443 |
| 2012/0041739 A1* | 2/2012 | Taylor | 703/11 |
| 2012/0101552 A1* | 4/2012 | Lazarewicz et al. | 607/62 |
| 2013/0030295 A1 | 1/2013 | Huennekens et al. | |
| 2013/0150734 A1* | 6/2013 | Orr et al. | 600/484 |
| 2013/0231554 A1 | 9/2013 | Jung | |
| 2013/0303888 A1* | 11/2013 | Deladi et al. | 600/424 |
| 2014/0039276 A1 | 2/2014 | Hattangadi et al. | |
| 2014/0088414 A1 | 3/2014 | Mittal et al. | |
| 2014/0249784 A1 | 9/2014 | Sankaran et al. | |
| 2015/0157259 A1 | 6/2015 | Bradu | |
| 2015/0324962 A1* | 11/2015 | Itu | G06T 7/00 382/130 |
| 2015/0359601 A1 | 12/2015 | Sauer et al. | |
| 2016/0228071 A1* | 8/2016 | Wang | A61B 5/6852 |

OTHER PUBLICATIONS

Vranckx et al. "Coronary Pressure-Derived Fractional Flow Reserve Measurements, Circulation: Cardiovascular Interventions" 2012;5:312-317, originally published Apr. 17, 2012.

* cited by examiner

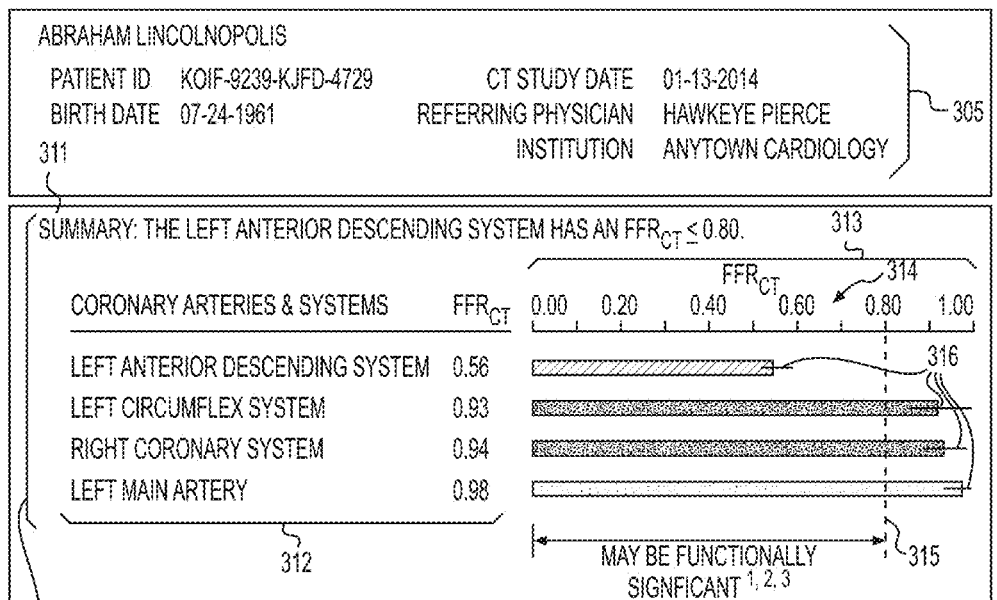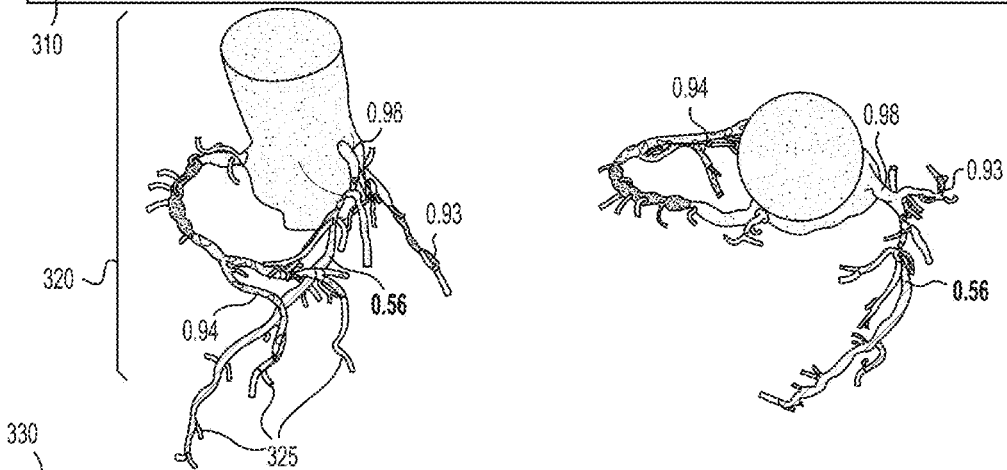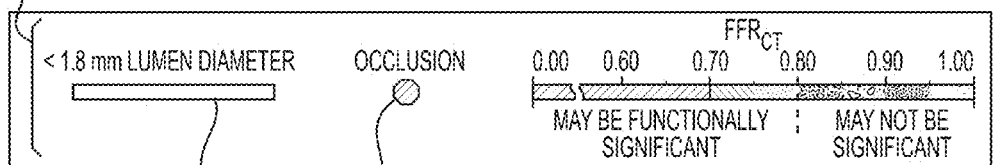
FIG. 3

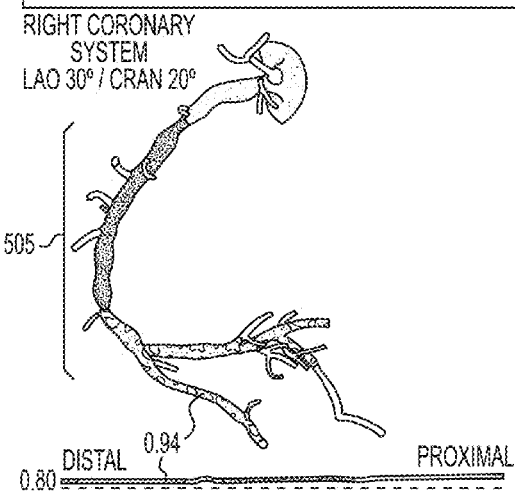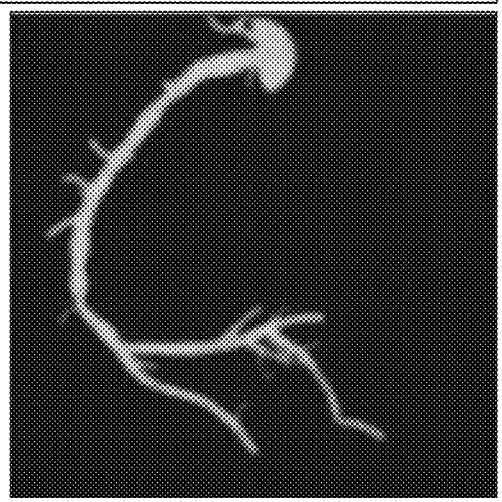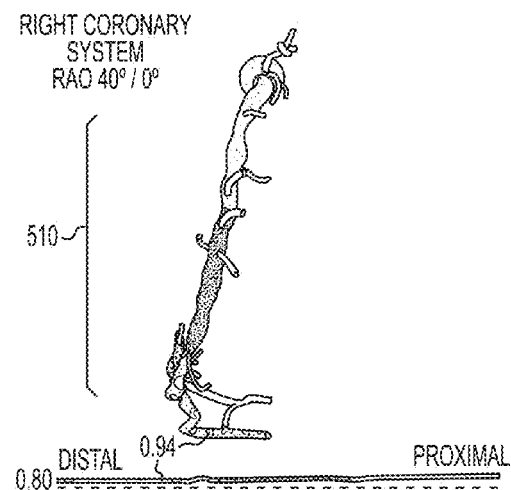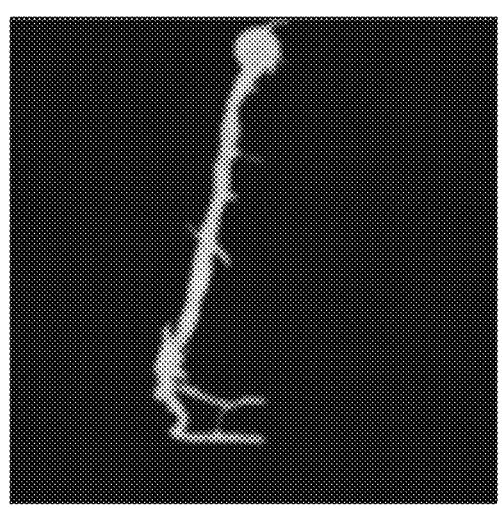
FIG. 5

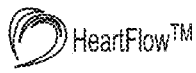HeartFlow™                                $FFR_{CT}$ RESULTS

ABRAHAM LINCOLNOPOLIS
PATIENT ID   KOIF-9239-KJFD-4729      CT STUDY DATE   01-13-2014
BIRTH DATE   07-24-1961                 REFERRING PHYSICIAN   HAWKEYE PIERCE
                                                    INSTITUTION   ANYTOWN CARDIOLOGY

FUNCTIONAL QUALITY SCORE:
THE FUCTIONAL QUALITY SCORE IS A QUANTITATIVE GAUGE OF THE EFFECT OF cCTA IMAGE QUALITY AND RESOLUTION ON THE ACCURACY OF COMPUTED FFRct VALUES.[5]

LEFT MAIN [EXCELLENT]
LEFT ANTERIOR DESCENDING SYSTEM [FAIR]
LEFT CIRCUMFLEX SYSTEM [GOOD]
RIGHT CORONARY SYSTEM [GOOD]   610

UNDERSTANDING THE SCORE
EXCELLENT: cCTA IMAGE QUALITY AND GEOMETRIC VARIABILITY DO NOT EFFECT THE FFRct ANALYSIS IN ANY SIGNIFICANT WAY.
GOOD: FEW ARTIFACTS OR GEOMETRIC VARIABILITY WERE FOUND IN THE cCTA STUDY TO EFFECT THE FFRct ANALYSIS.
FAIR: A MODERATE AMOUNT OF ARTIFACTS AND GEOMETRIC VARIABILITY WERE FOUND IN THE cCTA STUDY TO EFFECT THE FFRct ANALYSIS.

WARNINGS & INFORMATION:
605

HEARTFLOW $FFR_{CT}$ ANALYSIS SIMULATES MAXIMAL MYOCARDINAL HYPEREMIA. INDUCTION OF MYOCARDIAL HYPEREMIA COMMONLY INCLUDES VASODILATION OF THE EPICARDIAL CORONARY ARTERIES VIA NITRATE ADMINISTRATION. THEREFORE, HEARTFLOW RECOMMENDS FOLLOWING SCCT GUIDELINES FOR cCTA ACQUISITION, WHICH INCLUDE THE USE OF SUBLINGUAL NITRATES AT THE TIME OF IMAGE ACQUISITION.[4] ABSENCE OF NITRATE ADMINISTRATION DURING cCTA ACQUISITION MAY ADVERSELY AFFECT THE ACCURACY OF THE $FFR_{CT}$ ANALYSIS.

DIAGNOSTIC PERFORMANCE OF FFRCT USING $FFR_{CATH}$ AS THE REFERENCE STANDARD IS: 86% ACCURATE, 84% SENSITIVE, AND 86% SPECIFIC.[3] REFER TO PRODUCT INSTRUCTIONS FOR USE FOR PATIENT POPULATIONS IN WHICH $FFR_{CT}$ HAS BEEN CLINICALLY EVALUATED, RELEVANT CLINICAL DATA, AND THE PRODUCT WARNINGS.

$FFR_{CT}$ FUNCTIONAL ANALYSIS SHOULD BE CONSIDERED IN CONJUNCTION WITH CUSTOMARY ANATOMIC ASSESSMENT OF THE FULL RANGE OF AVAILABLE cCTA IMAGES. STUDIES HAVE SHOWN THAT TREATMENT GUIDED BY $FFR_{CATH}$ RESULTS IN IMPROVED CLINICAL OUTCOMES, INCLUDING A SIGNIFICATLY REDUCED RISK OF DEATH OR MAJOR CARDIAC EVENTS, AND LOWER HEALTHCARE COSTS. REVASCULARIZATION OF CORONARY ARTERY STENOSES WITH $FFR_{CATH}$ OF $\leq 0.80$ MAY RESULT IN IMPROVED CLINICAL OUTCOMES.[1,2]
615

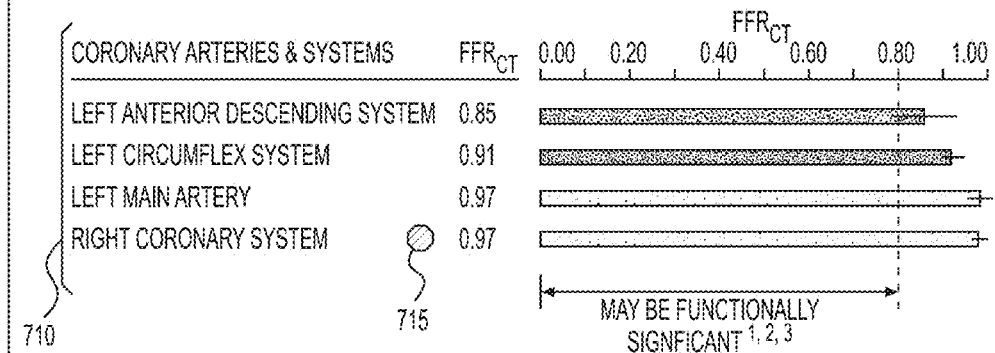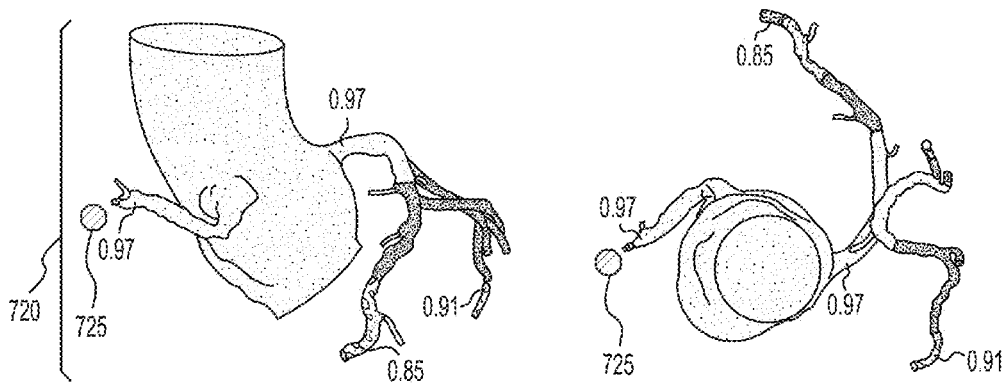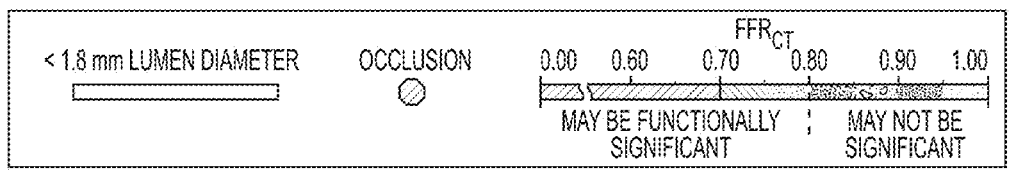
FIG. 7

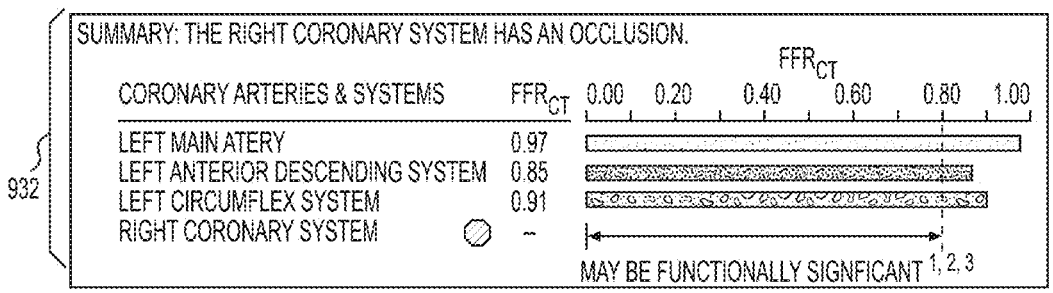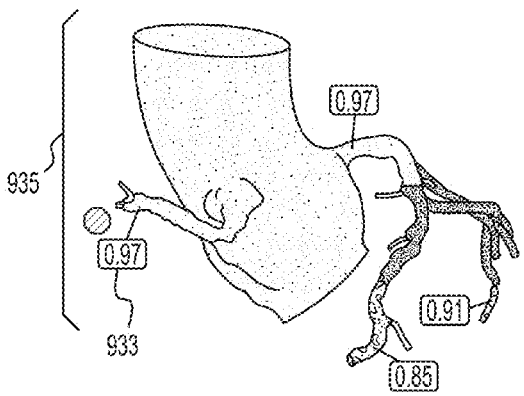
FIG. 9C
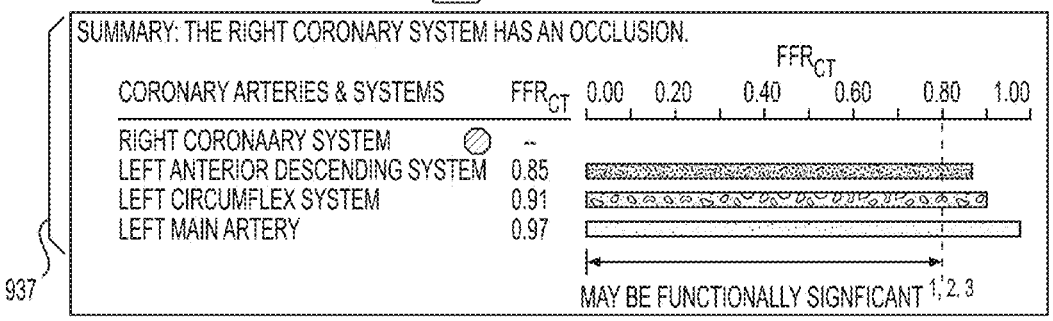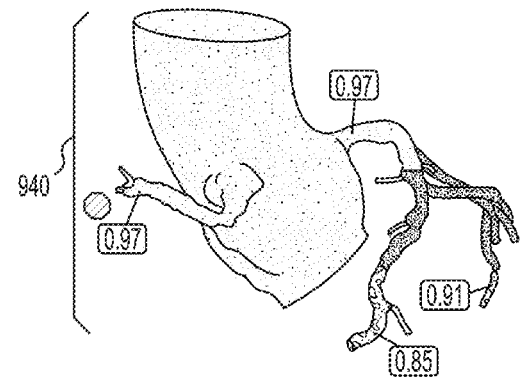
FIG. 9D

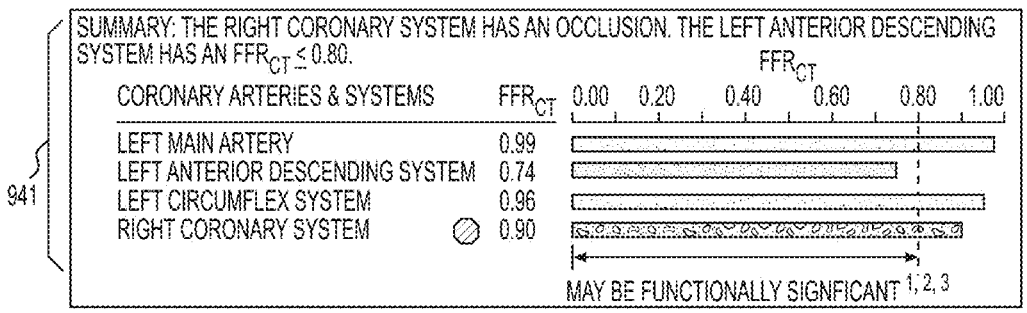
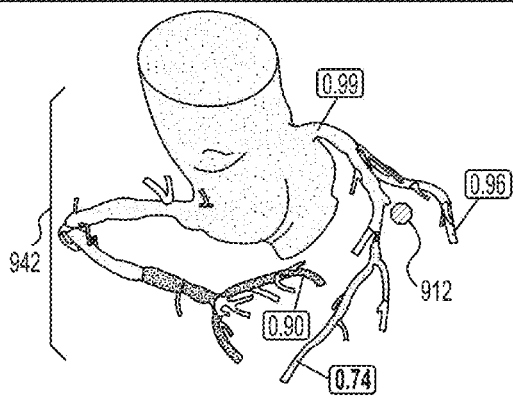
*FIG. 9E*
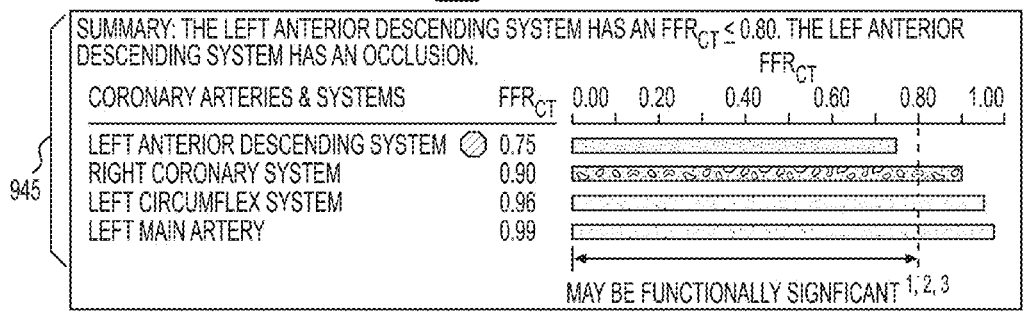
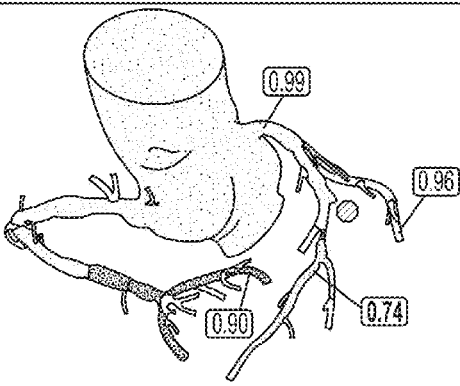
*FIG. 9F*

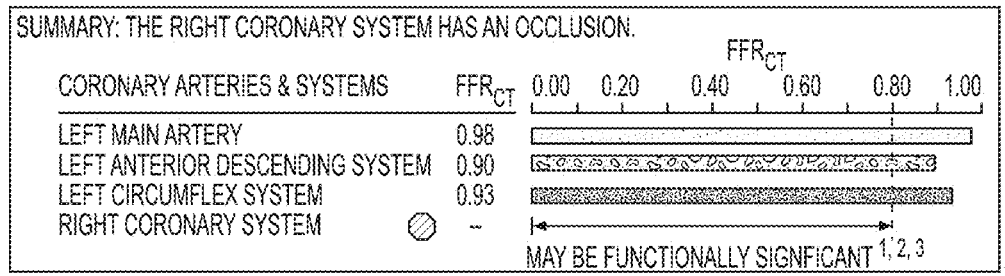
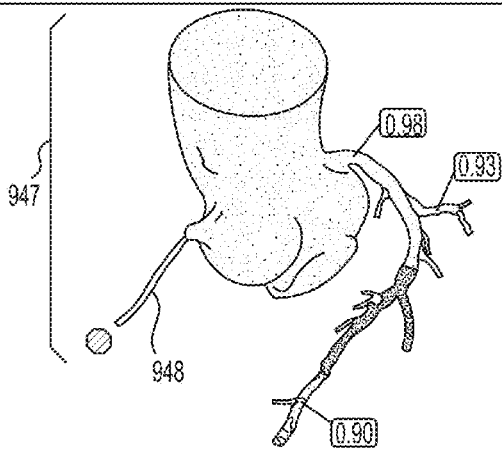
*FIG. 9G*
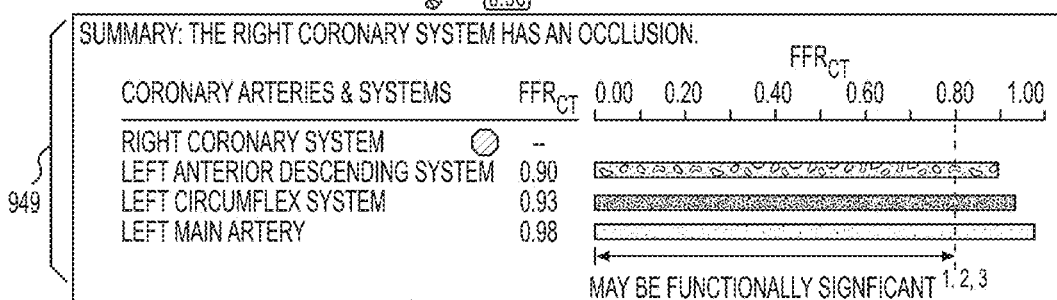
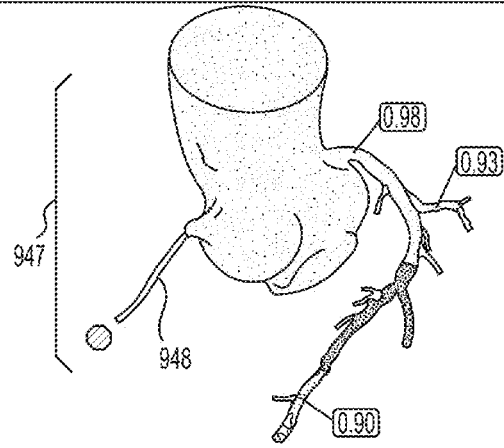
*FIG. 9H*

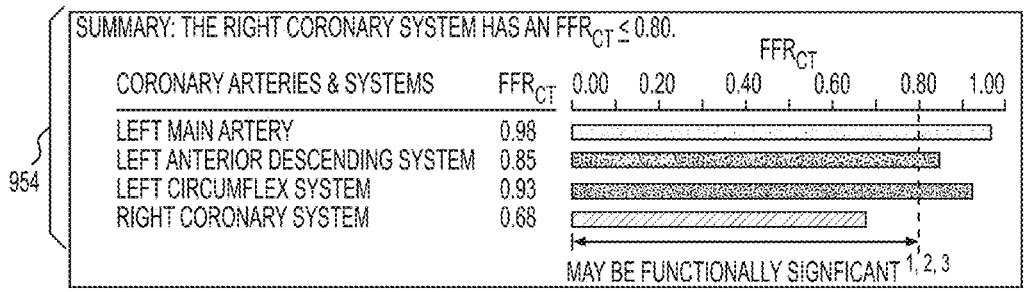
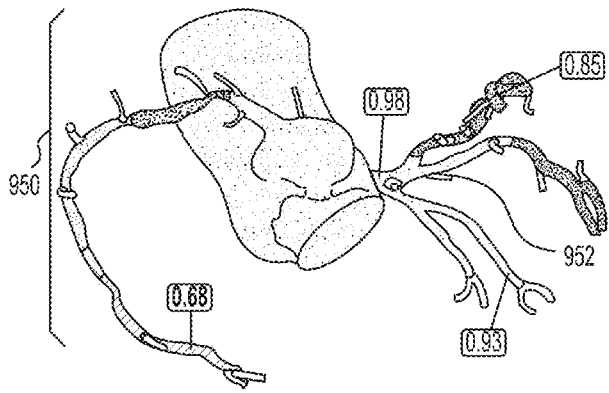
FIG. 9I
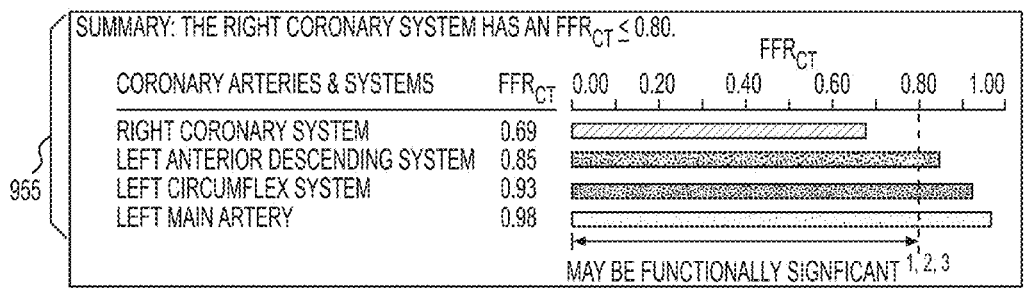
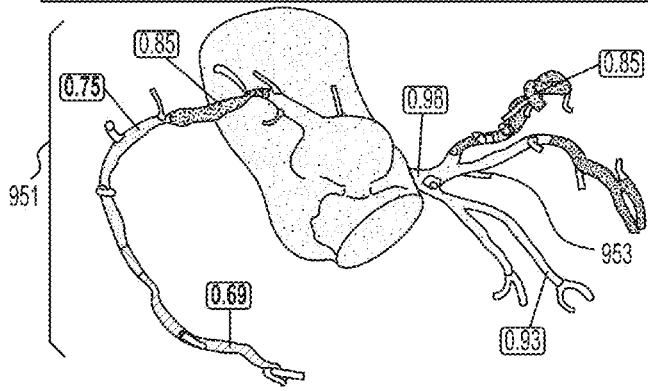
FIG. 9J

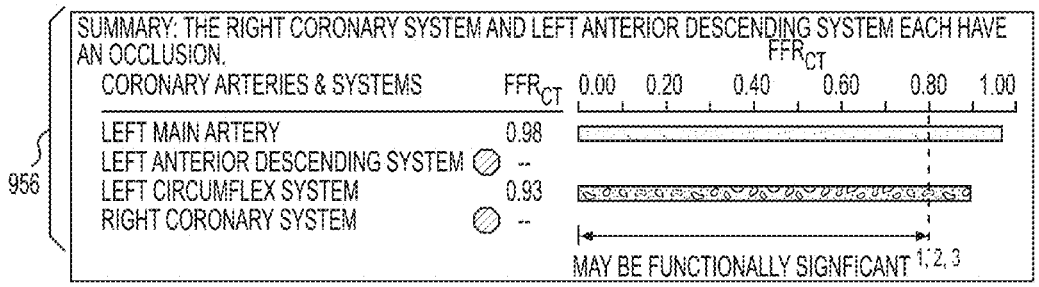
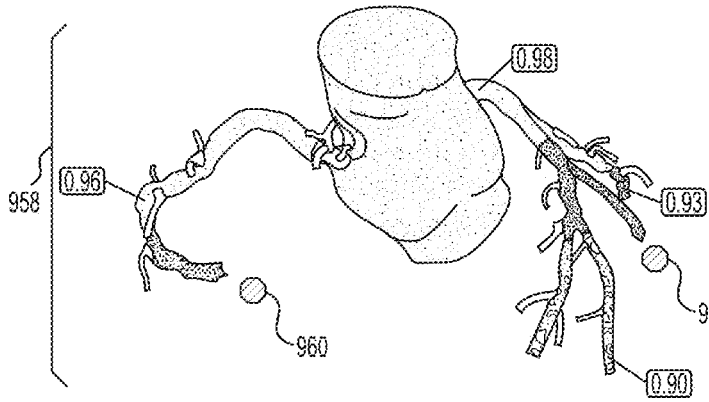
FIG. 9K
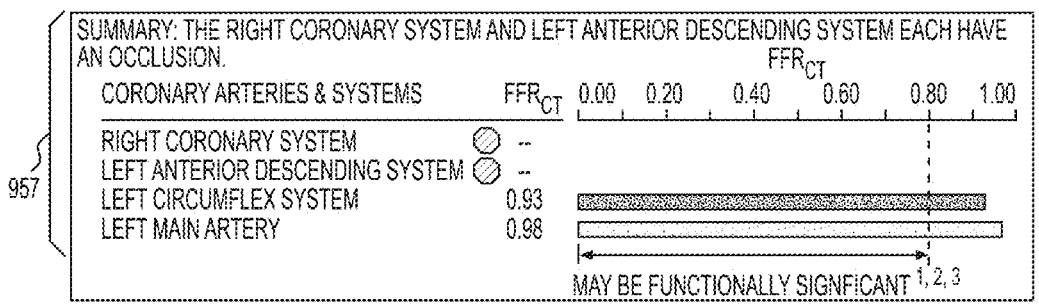
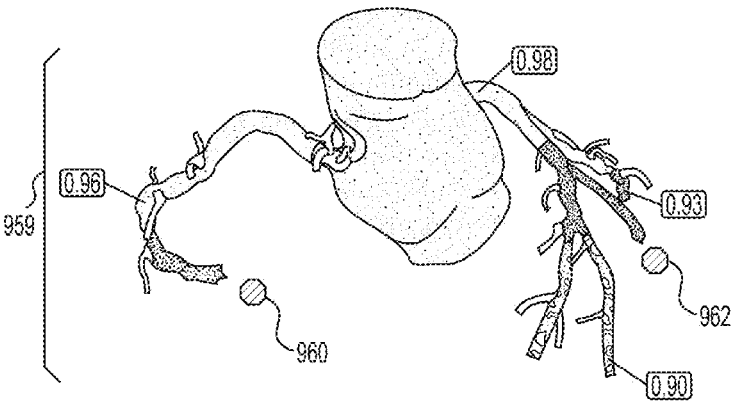
FIG. 9L

ARKANSAS

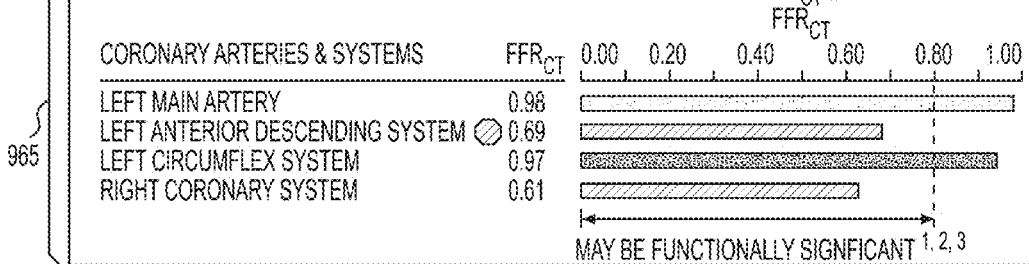

SUMMARY: THE LEFT ANTERIOR DESCENDING SYSTEM HAS AN OCCLUSION. THE RIGHT CORONARY SYSTEM AND THE LEFT ANTERIOR DESCENDING SYSTEM EACH HAVE AN $FFR_{CT} \leq 0.80$.

| CORONARY ARTERIES & SYSTEMS | $FFR_{CT}$ | 0.00 | 0.20 | 0.40 | 0.60 | 0.80 | 1.00 |
|---|---|---|---|---|---|---|---|
| LEFT MAIN ARTERY | 0.98 | | | | | | |
| LEFT ANTERIOR DESCENDING SYSTEM | 0.69 | | | | | | |
| LEFT CIRCUMFLEX SYSTEM | 0.97 | | | | | | |
| RIGHT CORONARY SYSTEM | 0.61 | | | | | | |

MAY BE FUNCTIONALLY SIGNFICANT [1,2,3]

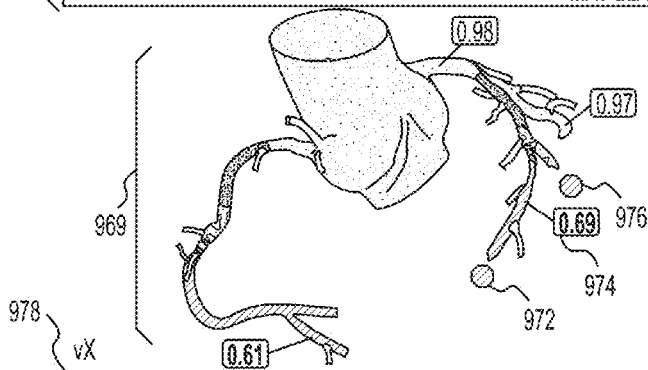

FIG. 9M

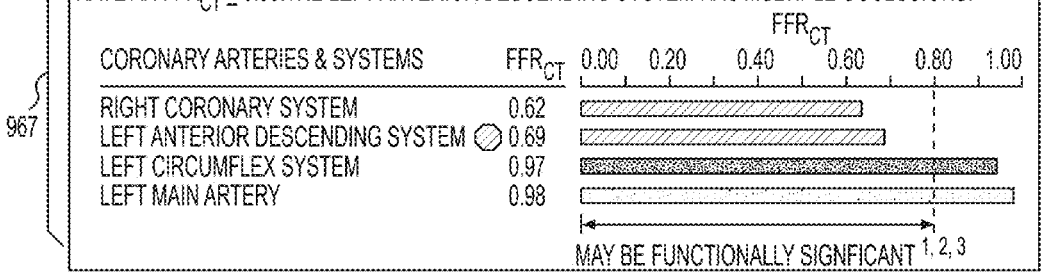

SUMMARY: THE RIGHT CORONARY SYSTEM AND THE LEFT ANTERIOR DESCENDING SYSTEM EACH HAVE AN $FFR_{CT} \leq 0.80$. THE LEFT ANTERIOR DESCENDING SYSTEM HAS MULTIPLE OCCLUSIONS.

| CORONARY ARTERIES & SYSTEMS | $FFR_{CT}$ | 0.00 | 0.20 | 0.40 | 0.60 | 0.80 | 1.00 |
|---|---|---|---|---|---|---|---|
| RIGHT CORONARY SYSTEM | 0.62 | | | | | | |
| LEFT ANTERIOR DESCENDING SYSTEM | 0.69 | | | | | | |
| LEFT CIRCUMFLEX SYSTEM | 0.97 | | | | | | |
| LEFT MAIN ARTERY | 0.98 | | | | | | |

MAY BE FUNCTIONALLY SIGNFICANT [1,2,3]

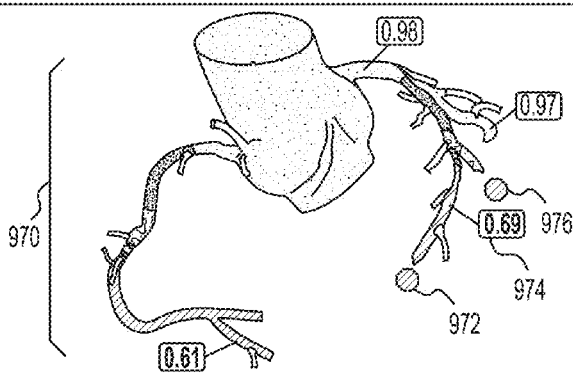

FIG. 9N

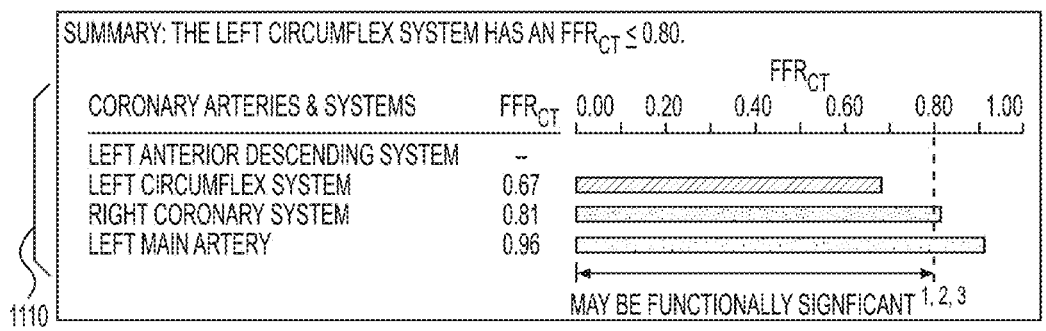
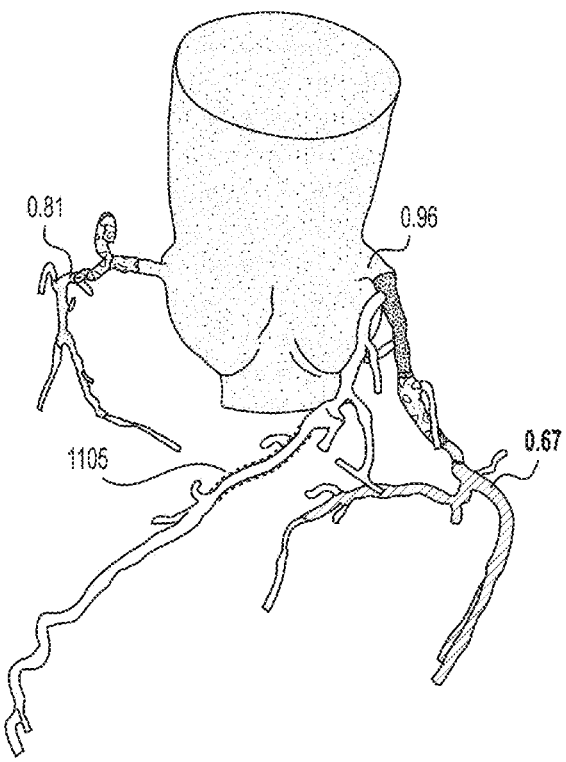
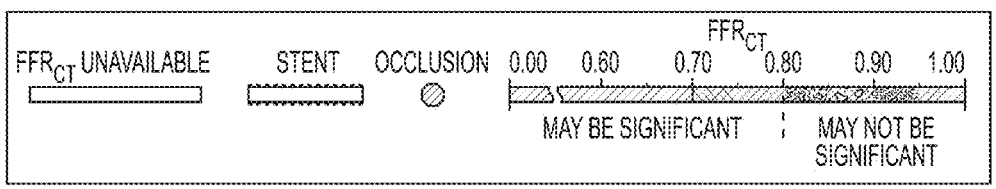
FIG. 11A

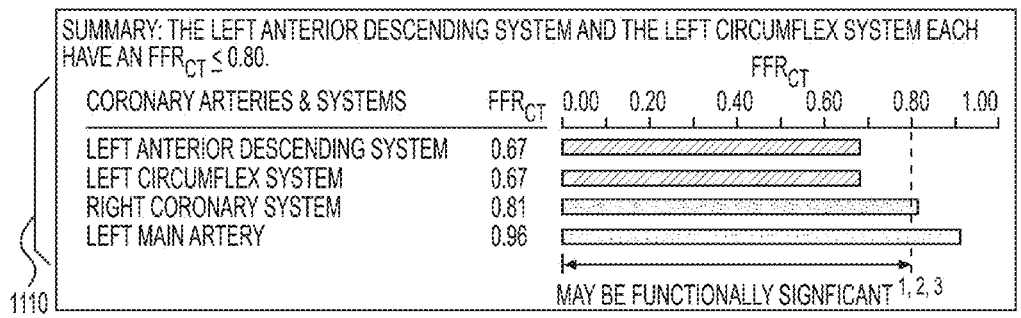
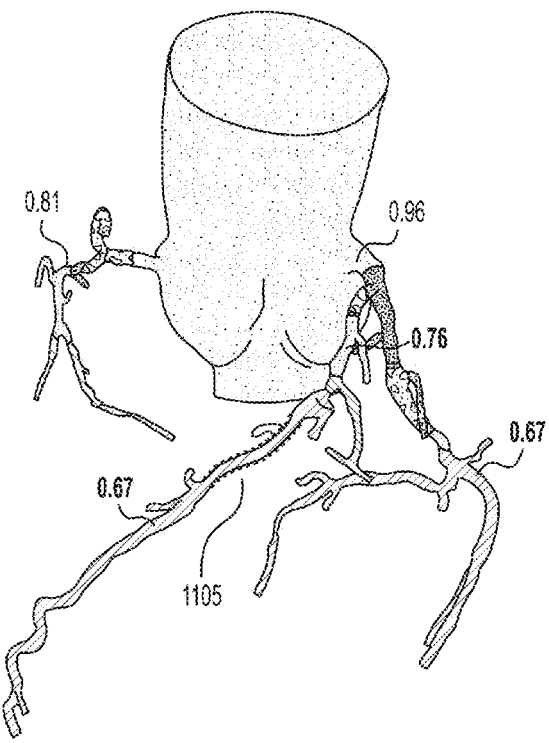
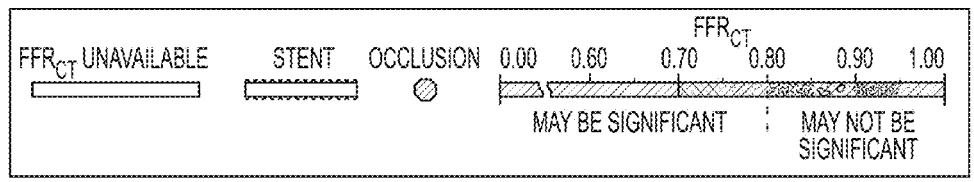
FIG. 11B

SYSTEMS AND METHODS FOR REPORTING BLOOD FLOW CHARACTERISTICS

RELATED APPLICATION

This application claims the benefit of priority from U.S. Provisional Application No. 62/005,272, filed May 30, 2014, which is hereby incorporated herein by reference in its entirety.

TECHNICAL FIELD

Embodiments include methods and systems for reporting patient-specific blood flow characteristics.

BACKGROUND

Coronary artery disease may produce coronary lesions in the blood vessels providing blood to the heart, such as a stenosis (abnormal narrowing of a blood vessel). As a result, blood flow to the heart may be restricted. A patient suffering from coronary artery disease may experience chest pain, referred to as chronic stable angina during physical exertion or unstable angina when the patient is at rest. A more severe manifestation of disease may lead to myocardial infarction, or heart attack.

A need exists to provide more accurate data relating to coronary lesions, e.g., size, shape, location, functional significance (e.g., whether the lesion impacts blood flow), etc. Patients suffering from chest pain and/or exhibiting symptoms of coronary artery disease may be subjected to one or more tests that may provide some indirect evidence relating to coronary lesions. For example, noninvasive tests may include electrocardiograms, biomarker evaluation from blood tests, treadmill tests, echocardiography, single positron emission computed tomography (SPECT), and positron emission tomography (PET). These noninvasive tests, however, typically do not provide a direct assessment of coronary lesions or assess blood flow rates. The noninvasive tests may provide indirect evidence of coronary lesions by looking for changes in electrical activity of the heart (e.g., using electrocardiography (ECG)), motion of the myocardium (e.g., using stress echocardiography), perfusion of the myocardium (e.g., using PET or SPECT), or metabolic changes (e.g., using biomarkers).

For example, anatomic data may be obtained noninvasively using coronary computed tomographic angiography (CCTA). CCTA may be used for imaging of patients with chest pain and involves using computed tomography (CT) technology to image the heart and the coronary arteries following an intravenous infusion of a contrast agent. However, CCTA also cannot provide direct information on the functional significance of coronary lesions, e.g., whether the lesions affect blood flow. In addition, since CCTA is purely a diagnostic test, it cannot be used to predict changes in coronary blood flow, pressure, or myocardial perfusion under other physiologic states, e.g., exercise, nor can it be used to predict outcomes of interventions.

Thus, patients may also require an invasive test, such as diagnostic cardiac catheterization, to visualize coronary lesions. Diagnostic cardiac catheterization may include performing conventional coronary angiography (CCA) to gather anatomic data on coronary lesions by providing a doctor with an image of the size and shape of the arteries. CCA, however, does not provide data for assessing the functional significance of coronary lesions. For example, a doctor may not be able to diagnose whether a coronary lesion is harmful without determining whether the lesion is functionally significant. Thus, CCA has led to what has been referred to as an "oculostenotic reflex" of some interventional cardiologists to insert a stent for every lesion found with CCA regardless of whether the lesion is functionally significant. As a result, CCA may lead to unnecessary operations on the patient, which may pose added risks to patients and may result in unnecessary heath care costs for patients.

During diagnostic cardiac catheterization, the functional significance of a coronary lesion may be assessed invasively by measuring the fractional flow reserve (FFR) of an observed lesion. FFR is defined as the ratio of the mean blood pressure downstream of a lesion divided by the mean blood pressure upstream from the lesion, e.g., the aortic pressure, under conditions of increased coronary blood flow, e.g., induced by intravenous administration of adenosine. The blood pressures may be measured by inserting a pressure wire into the patient. Thus, the decision to treat a lesion based on the determined FFR may be made after the initial cost and risk of diagnostic cardiac catheterization has already been incurred.

Thus, a need exists for a method for assessing coronary anatomy, myocardial perfusion, and coronary artery flow noninvasively. Such a method and system may benefit cardiologists who diagnose and plan treatments for patients with suspected coronary artery disease. In addition, a need exists for a method to predict coronary artery flow and myocardial perfusion under conditions that cannot be directly measured, e.g., exercise, and to predict outcomes of medical, interventional, and surgical treatments on coronary artery blood flow and myocardial perfusion. In addition, a need exists to generate and display reports relating to patient-specific blood flow characteristics.

The foregoing general description and the following detailed description are exemplary and explanatory only and are not restrictive of the disclosure.

SUMMARY

In accordance with an embodiment, a system displays cardiovascular information for a patient. The system may include at least one computer system configured to receive patient-specific data regarding a geometry of the patient's heart and create a model representing at least a portion of the patient's heart based on the patient-specific data. The computer system may determine at least one value of the blood flow characteristic within the patient's heart based on the model. The computer system may also display a report comprising a representation of at least one artery corresponding to at least a portion the model, and display one or more indicators of the value of the blood flow characteristic on a corresponding portion of the at least one artery.

In accordance with another embodiment, a method displays cardiovascular information for a patient. The method may include receiving patient-specific data regarding a geometry of the patient's heart, and creating a model representing at least a portion of the patient's heart based on the patient-specific data. The method may also include determining at least one value of the blood flow characteristic within the patient's heart based on the model. The method may further include displaying a report comprising a representation of at least one artery corresponding to at least a portion the model, and displaying one or more indicators of the value of the blood flow characteristic on a corresponding portion of the at least one artery.

In accordance with another embodiment, a non-transitory computer-readable medium may store instructions that, when executed by a processor, cause the processor to perform a method for displaying cardiovascular information of a patient. The method may include receiving patient-specific data regarding a geometry of the patient's heart, and creating a model representing at least a portion of the patient's heart based on the patient-specific data. The method may also include determining at least one value of the blood flow characteristic within the patient's heart based on the model. The method may further include displaying a report comprising a representation of at least one artery corresponding to at least a portion the model, and displaying one or more indicators of the value of the blood flow characteristic on a corresponding portion of the at least one artery.

Additional embodiments and advantages will be set forth in part in the description that follows, including the attached appendix, and in part will be obvious from the description, or may be learned by practice of the disclosure. The embodiments and advantages will be realized and attained by means of the elements and combinations particularly pointed out below.

BRIEF DESCRIPTION OF THE DRAWINGS

The accompanying drawings, which are incorporated in and constitute a part of this specification, illustrate several embodiments and together with the description, serve to explain the principles of the disclosure.

FIG. 3 shows an example report summary of a medical imaging report which may be generated by a software tool;

FIG. 5 shows additional example of artery details that may be included in a medical imaging report;

FIG. 6 depicts an example report conclusion of a medical imaging report;

FIG. 7 depicts an example portion of a medical imaging report which may display indicators of one or more arterial occlusions;

FIGS. 11A-11B show an example report summary of a medical imaging report which displays a stent;

DESCRIPTION OF THE EMBODIMENTS

Reference will now be made in detail to exemplary embodiments, examples of which are illustrated in the accompanying drawings. Wherever possible, the same reference numbers will be used throughout the drawings to refer to the same or like parts.

In an exemplary embodiment, a method and system determines various information relating to blood flow in a specific patient using information retrieved from the patient noninvasively. Various embodiments of such a method and system are described in greater detail in U.S. Pat. No. 8,315,812 to Charles A. Taylor, filed Jan. 25, 2011, and entitled "Method and System for Patient-Specific Modeling of Blood Flow," which is assigned to the assignee of the present application and which is hereby incorporated by reference in its entirety.

In some embodiments, the information determined by the method and system may relate to blood flow in the patient's coronary vasculature. Alternatively, the determined information may relate to blood flow in other areas of the patient's vasculature, such as carotid, peripheral, abdominal, renal, and/or cerebral vasculature. The coronary vasculature includes a complex network of vessels ranging from large arteries to arterioles, capillaries, venules, veins, etc. The coronary vasculature circulates blood to and within the heart and includes an aorta that supplies blood to a plurality of main coronary arteries (e.g., the left anterior descending (LAD) artery, the left circumflex (LCX) artery, the right coronary (RCA) artery, etc.), which may further divide into branches of arteries or other types of vessels downstream from the aorta and the main coronary arteries. Thus, the exemplary method and system may determine various information relating to blood flow within the aorta, the main coronary arteries, and/or other coronary arteries or vessels downstream from the main coronary arteries. Although the aorta and coronary arteries (and the branches that extend therefrom) are discussed below, the disclosed method and system may also apply to other types of vessels.

In an exemplary embodiment, the information determined by the disclosed methods and systems may include, but is not limited to, various blood flow characteristics or parameters, such as blood flow velocity, pressure (or a ratio thereof), flow rate (or ratio thereof), and FFR at various locations in the aorta, the main coronary arteries, and/or other coronary arteries or vessels downstream from the main coronary arteries. This information may be used to determine whether a lesion is functionally significant and/or whether to treat the lesion. This information may be determined using information obtained noninvasively from the patient. As a result, the decision whether to treat a lesion may be made without the cost and risk associated with invasive procedures.

Figure 1:
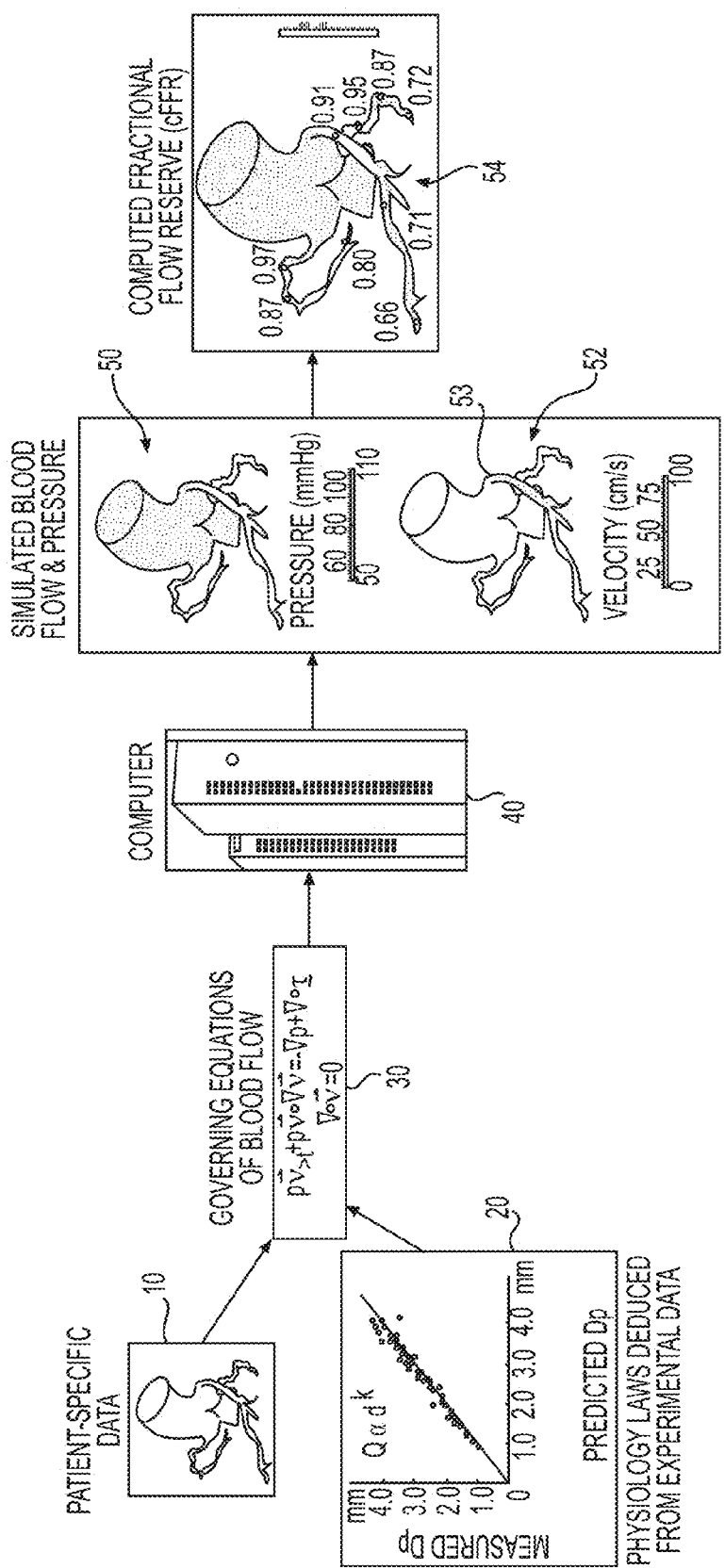
FIG. 1 is a schematic diagram of a system for providing various information relating to coronary blood flow in a specific patient, according to an exemplary embodiment.

FIG. 1 shows aspects of a system for providing various information relating to coronary blood flow in a specific patient, according to an exemplary embodiment. A three-dimensional model 10 of the patient's anatomy may be created using data obtained noninvasively from the patient as will be described below in more detail. Other patient-specific information may also be obtained noninvasively. In an exemplary embodiment, the portion of the patient's anatomy that is represented by the three-dimensional model 10 may include at least a portion of the aorta and a proximal portion of the main coronary arteries (and the branches extending or emanating therefrom) connected to the aorta.

Various physiological laws or relationships 20 relating to coronary blood flow may be deduced, e.g., from experimental data as will be described below in more detail. Using the three-dimensional anatomical model 10 and the deduced physiological laws 20, a plurality of equations 30 relating to coronary blood flow may be determined as will be described below in more detail. For example, the equations 30 may be determined and solved using any numerical method, e.g., finite difference, finite volume, spectral, lattice Boltzmann, particle-based, level set, finite element methods, etc. The equations 30 may be solvable to determine information (e.g., pressure, velocity, FFR, etc.) about the coronary blood flow in the patient's anatomy at various points in the anatomy represented by the model 10.

The equations 30 may be solved using a computer 40. Based on the solved equations, the computer 40 may output one or more images or simulations indicating information relating to the blood flow in the patient's anatomy represented by the model 10. For example, the image(s) may include a simulated blood pressure model 50, a simulated blood flow or velocity model 52, a computed FFR (cFFR) model 54, etc., as will be described in further detail below. The simulated blood pressure model 50, the simulated blood flow model 52, and the cFFR model 54 provide information regarding the respective pressure, velocity, and cFFR at various locations along three dimensions in the patient's anatomy represented by the model 10. cFFR may be calculated as the ratio of the blood pressure at a particular location in the model 10 divided by the blood pressure in the aorta, e.g., at the inflow boundary of the model 10, under conditions of increased coronary blood flow, e.g., conventionally induced by intravenous administration of adenosine.

In an exemplary embodiment, the computer 40 may include one or more non-transitory computer-readable storage devices that store instructions that, when executed by a processor, computer system, etc., may perform any of the actions described herein for providing various information relating to blood flow in the patient. The computer 40 may include a desktop or portable computer, a workstation, a server, a personal digital assistant, or any other computer system. The computer 40 may include a processor, a read-only memory (ROM), a random access memory (RAM), an input/output (I/O) adapter for connecting peripheral devices (e.g., an input device, output device, storage device, etc.), a user interface adapter for connecting input devices such as a keyboard, a mouse, a touch screen, a voice input, and/or other devices, a communications adapter for connecting the computer 40 to a network, a display adapter for connecting the computer 40 to a display, etc. For example, the display may be used to display the three-dimensional model 10 and/or any images generated by solving the equations 30, such as the simulated blood pressure model 50, the simulated blood flow model 52, and/or the cFFR model 54. In another exemplary embodiment, the computer 40 may be a plurality of computers that share the functions performed when generating the cFFR and/or other blood flow characteristics. For example, information indicating blood flow characteristics and a reduced-order model for modeling treatment options may be provided to a tablet computer for further processing.

Figure 2:
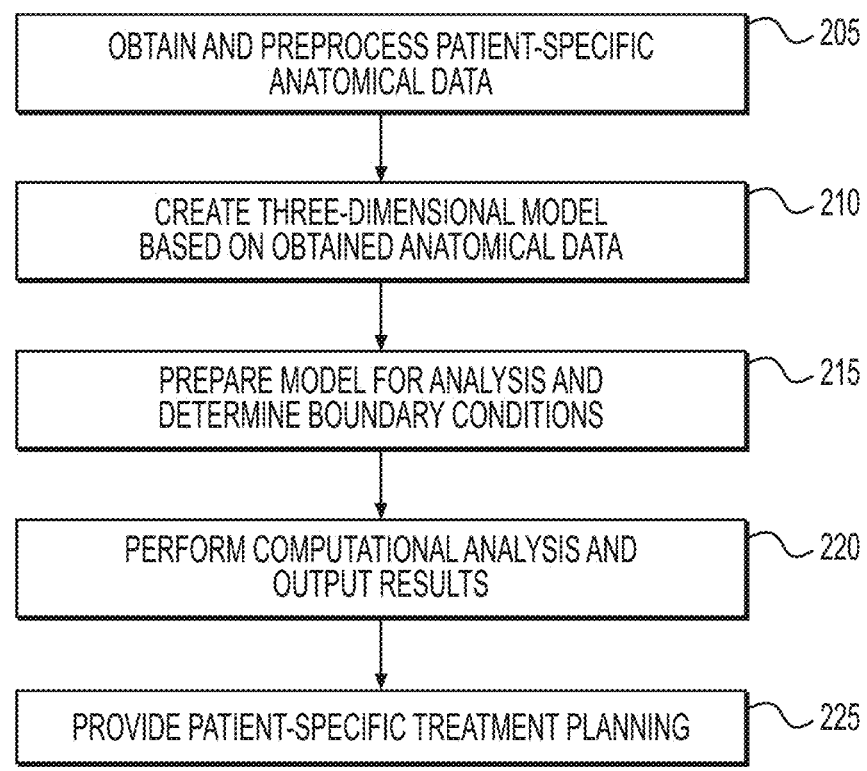
FIG. 2 is a flow chart of a method for providing various information relating to blood flow in a specific patient, according to an exemplary embodiment.

FIG. 2 shows aspects of a method for providing various information relating to blood flow in a specific patient, according to another exemplary embodiment. The method may include obtaining patient-specific anatomical data, such as information regarding the patient's anatomy (e.g., at least a portion of the aorta and a proximal portion of the main coronary arteries (and the branches extending therefrom) connected to the aorta), and preprocessing the data (step 205). The patient-specific anatomical data may be obtained noninvasively, e.g., by CCTA.

A three-dimensional model of the patient's anatomy may be created based on the obtained anatomical data (step 210). For example, the three-dimensional model may be the three-dimensional model 10 of the patient's anatomy described above in connection with FIG. 1.

The three-dimensional model may be prepared for analysis and boundary conditions may be determined (step 215). For example, the three-dimensional model 10 of the patient's anatomy described above in connection with FIG. 1 may be trimmed and discretized into a volumetric mesh, e.g., a finite element or finite volume mesh. The volumetric mesh may be used to generate the equations 30 described above in connection with FIG. 1.

Boundary conditions may also be assigned and incorporated into the equations 30 described above in connection with FIG. 1. The boundary conditions provide information about the three-dimensional model 10 at its boundaries, e.g., inflow boundaries, outflow boundaries, vessel wall boundaries, etc. The inflow boundaries may include the boundaries through which flow is directed into the anatomy of the three-dimensional model, such as at an end of the aorta near the aortic root. Each inflow boundary may be assigned, e.g., with a prescribed value or field for velocity, flow rate, pressure, or other characteristic, by coupling a heart model and/or a lumped parameter model to the boundary, etc. The outflow boundaries may include the boundaries through which flow is directed outward from the anatomy of the three-dimensional model, such as at an end of the aorta near the aortic arch, and the downstream ends of the main coronary arteries and the branches that extend therefrom. Each outflow boundary can be assigned, e.g., by coupling a lumped parameter or distributed (e.g., a one-dimensional wave propagation) model. The prescribed values for the inflow and/or outflow boundary conditions may be determined by noninvasively measuring physiologic characteristics of the patient, such as, but not limited to, cardiac output (the volume of blood flow from the heart), blood pressure, myocardial mass, etc. The vessel wall boundaries may include the physical boundaries of the aorta, the main coronary arteries, and/or other coronary arteries or vessels of the three-dimensional model 10.

The computational analysis may be performed using the prepared three-dimensional model and the determined boundary conditions (step 220) to determine blood flow information for the patient. For example, the computational analysis may be performed with the equations 30 and using the computer 40 described above in connection with FIG. 1 to produce the images described above in connection with FIG. 1, such as the simulated blood pressure model 50, the simulated blood flow model 52, and/or the cFFR model 54.

The method may also include providing patient-specific treatment options using the results (step 225). For example, the three-dimensional model 10 created in step 210 and/or the boundary conditions assigned in step 215 may be adjusted to model one or more treatments, e.g., placing a coronary stent in one of the coronary arteries represented in the three-dimensional model 10 or other treatment options. Then, the computational analysis may be performed as described above in step 220 in order to produce new images, such as updated versions of the blood pressure model 50, the blood flow model 52, and/or the cFFR model 54. These new images may be used to determine a change in blood flow velocity and pressure if the treatment option(s) are adopted.

The systems and methods disclosed herein may be incorporated into a software tool accessed by physicians to provide a noninvasive means to quantify blood flow in the coronary arteries and to assess the functional significance of coronary artery disease. In addition, physicians may use the software tool to predict the effect of medical, interventional, and/or surgical treatments on coronary artery blood flow.

The software tool may prevent, diagnose, manage, and/or treat disease in other portions of the cardiovascular system including arteries of the neck (e.g., carotid arteries), arteries in the head (e.g., cerebral arteries), arteries in the thorax, arteries in the abdomen (e.g., the abdominal aorta and its branches), arteries in the arms, or arteries in the legs (e.g., the femoral and popliteal arteries). The software tool may be interactive to enable physicians to develop optimal personalized therapies for patients.

For example, the software tool may be incorporated at least partially into a computer system, e.g., the computer 40 shown in FIG. 1 used by a physician or other user. The computer system may receive data obtained noninvasively from the patient (e.g., data used to create the three-dimensional model 10, data used to apply boundary conditions or perform the computational analysis, etc.). For example, the data may be input by the physician or may be received over a network, such as the Internet, from another source capable of accessing and providing such data, such as a radiology or other medical lab. The data may be transmitted via a network or other system for communicating the data, or directly into the computer system. The software tool may use the data to produce and display the three-dimensional model 10 or other models/meshes and/or any simulations or other results determined by solving the equations 30 described above in connection with FIG. 1, such as the simulated blood pressure model 50, the simulated blood flow model 52, and/or the cFFR model 54. Thus, the software tool may perform steps 205-225. In step 225, the physician may provide further inputs to the computer system to select possible treatment options, and the computer system may display to the physician new simulations based on the selected possible treatment options. Further, each of steps 205-225 shown in FIG. 2 may be performed using separate software packages or modules.

Alternatively, the software tool may be provided as part of a web-based service or other service, e.g., a service provided by an entity that is separate from the physician. The service provider may, for example, operate the web-based service and may provide a web portal or other web-based application (e.g., run on a server or other computer system operated by the service provider) that is accessible to physicians or other users via a network or other methods of communicating data between computer systems. For example, the data obtained noninvasively from the patient may be provided to the service provider, and the service provider may use the data to produce the three-dimensional model 10 or other models/meshes and/or any simulations or other results determined by solving the equations 30 described above in connection with FIG. 1, such as the simulated blood pressure model 50, the simulated blood flow model 52, and/or the cFFR model 54. Then, the web-based service may transmit information relating to the three-dimensional model 10 or other models/meshes and/or the simulations so that the three-dimensional model 10 and/or the simulations may be displayed to the physician on the physician's computer system. Thus, the web-based service may perform steps 205-225 and any other steps described below for providing patient-specific information. In step 225, the physician may provide further inputs, e.g., to select possible treatment options or make other adjustments to the computational analysis, and the inputs may be transmitted to the computer system operated by the service provider (e.g., via the web portal). The web-based service may produce new simulations or other results based on the selected possible treatment options, and may communicate information relating to the new simulations back to the physician so that the new simulations may be displayed to the physician.

FIG. 3 shows an example report summary 300 of a medical imaging report for one or more patient-specific blood flow characteristics and/or artery characteristics which may be generated by the software tool. A medical imaging report may display one or more portions of the three-dimensional model 10 of the patient's anatomy, and data from the cFFR model generated by solving the equations 30. Models of a higher or reduced-order may also be displayed and/or any images and/or data generated by solving the equation 30, such as the simulated blood pressure model 50, and/or the simulated blood flow model 52. Example portions of a medical imaging report will now be discussed.

A summary header 305 is shown which may list data relevant to the patient, physician, imaging results, institution, etc. Fields listed may include the patient's name, birthdate, a patient identifier, the type and date of the imaging, the name and/or identifying information of the referring physician, and the name and/or other information associated with the referring institution, although other data relevant to the patient, physician, patient imaging, and institution may be displayed.

A summary box 310 may also be included in the report summary 300 which may automatically include a list of one or more arteries and the values of one or more associated blood flow characteristics. For example, the summary box 310 may display cFFR data for each major cardiac artery.

The summary box 310 may contain a summary line 311, which may contain information that is automatically determined to be important. Important information may include any information that may influence diagnosis and treatment of the patient, such as when a patient-specific blood flow characteristic is beyond a predetermined threshold. For example, a cFFR of 0.80 indicates that a stenosis has caused a 20% drop in blood pressure, and may be set as a predetermined threshold indicating that a lesion may be hemodynamically (functionally) significant. In one embodiment, any cardiac arteries with a cFFR less than or equal to 0.80 (or any other agreed-upon or predetermined standardized threshold, e.g., 0.7, 0.9, etc.) may be reported in the summary line 311. The summary box may also report the specific coronary artery or system related to the important information.

The summary box 310 may also contain a summary list 312 of cardiac arteries and/or systems along with one or more values of associated patient-specific blood flow characteristics. The values listed may be those automatically determined to be important, for example, values that most affect the diagnosis and treatment of the patient, as discussed above. For example, the lowest cFFR value for a main coronary artery system may be displayed. Cardiac arteries that are healthy and/or have patient-specific blood flow characteristics that do not meet a predetermined threshold may not necessarily be displayed in the summary box 310.

The listed arteries and/or arterial systems in the summary list 312 may be ordered by the likely or likelihood of functional significance of cFFR, although the list may be ordered by severity for any patient-specific blood flow characteristic.

The list of cardiac arteries and/or systems in the summary box 310 may be determined dynamically based on patient-specific blood flow characteristics. For example, if the arteries of the right coronary system have cFFR values that do not meet a predetermined functionally significant threshold of 0.80, the summary list 312 may list the lowest cFFR value in the system, but not specifically enumerate other arteries in the system, such as the right posterior descending artery or the right marginal artery. Conversely, the left coronary system may have one or more arteries and/or systems that have a patient-specific blood flow characteristic beyond a predetermined threshold, which may cause more of the arteries in the left coronary system to be specifically enumerated in the summary list 312. For example, the left anterior descending (LAD) system may have a cFFR of 0.56, below the predetermined threshold value of functional significance of 0.80, which may cause the LAD to be listed specifically in the summary list 312 separate from the left main (LM) artery, and the left circumflex (LCx) systems.

The list of cardiac arteries and/or systems in the summary box 310 may also be automatically ordered, with arterial systems containing more important patient-specific blood flow characteristics displayed more prominently. For example, the system containing the most functionally significant cFFR value may be displayed at the top of the summary list 312. The cardiac arteries and/or systems displayed in the summary box 310 may also be ordered alphabetically, by proximity to the aorta or other major cardiac arteries, by average arterial diameter or volume, by the importance of the artery to the health of the patient, and in any manner by patient-specific blood flow characteristic values, including by functional significance.

The summary box 310 may also comprise a summary graph 313, which may be displayed in association with the summary list 312. The summary graph 313 may display values associated with one or more patient-specific blood flow characteristics. For example, the most functionally significant cFFR value for each of the cardiac arteries and/or systems in the summary box 310 may be displayed as a bar graph. The size of each bar in the bar graph may correspond to the cFFR value or other blood flow characteristic value. Each bar in the summary graph 313 may be depicted as a certain color based on the cFFR value. Bars, lines, points and/or any other graph portions associated with cardiac arteries and/or systems with functionally significant lesions may be colored yellow, orange, red, and/or any color which acts as a warning. Conversely, bars, lines, points and/or or other graph portions associated with arteries without functionally significant lesions may be colored green, blue, purple, and/or some other color which indicates that that any lesions may not be functionally significant. Each bar may be colored according to the most functionally significant lesion in the associated artery and/or system. The summary graph 313 may be depicted as any of a variety of types of graphs, or even a combination of graph types, as will be discussed further herein. In the medical imaging report, values of patient-specific blood flow characteristics such as cFFR may be depicted using types of indicators other than, or in addition to, color.

Numerical values of the bars in the summary graph 313 may be indicated on or proximate to each bar, and/or indicated on an axis 314. A predetermined functional significance point 315 may also be indicated on the summary graph 313.

Uncertainties in the geometry of the patient's heart, boundary conditions, the three-dimensional model, and other uncertainties in patient-specific data may create uncertainties in the output simulations and models. These uncertainties 316 may be quantified and displayed on the summary graph 313, or anywhere in the medical imaging report. As shown in FIG. 3, the uncertainty range or confidence interval 316 may be displayed on the summary graph 313 overlapping with or adjacent to the associated bars in the summary graph 313. For example, if the most functionally significant cFFR value is 0.56 for an artery, the cFFR value may be displayed in the summary graph 313. The uncertainty associated with the cFFR may be plus or minus some value, e.g. 0.03 in this case. A line or other indicator corresponding to the 0.06 cFFR uncertainty range 316 may be placed over and/or proximate to the cFFR value bar in the summary graph 313. The uncertainty range 316 may be selectively displayed. For example, the uncertainty range 316 may be displayed when the associated value of a patient-specific blood flow characteristic exceeds a predetermined threshold. The uncertainty range 316 may also be displayed if the uncertainty renders it unclear whether or not a predetermined threshold has been reached.

The report summary 300 may also display a summary view 320, which may display at least a portion of one or more three-dimensional models 10. Each view may display a different angulation or point of view of the three-dimensional model 10. The summary view 320 may also display multiple views of one or more three-dimensional models 10. Each display within the summary view 320 may be colored, patterned, and/or visually indicated according to the determined patient-specific blood flow characteristics displayed in the summary box 310. For example, if the most functionally significant cFFR value in the LAD System is 0.56, in the summary view 320, the entire LAD System may be colored red, and the actual location of the lesion may be indicated with a pin, although other indicators may be used. Indicators may also be placed downstream from a lesion to indicate the effects of the lesion on the downstream portion of a vessel. Alternatively, arteries and/or systems in the summary view 320 may be colored, patterned, and/or visually indicated based on the blood flow characteristic at that location. For example, each point in the LAD system may be colored based upon the local corresponding cFFR value, rather than the entire LAD system being depicted as red. If a given artery or system has more than one functionally significant lesion, multiple pins or other indicators may be placed. Any pins or other indicators with values that exceed a predetermined threshold may be indicated more prominently. For example, each cFFR value below a functionally significant threshold of 0.80 may be displayed larger and/or in bold. Each artery or system in the summary box 310 may have one or more corresponding representations in the summary view 320.

The one or more views in the summary view 320 may be independently rotatable by the user, so that the user may obtain a desired point of view. Additionally, a user may zoom in or out on a portion of a view in the summary view 320, which may cause all views to zoom in or out in a corresponding manner. For example, a user may zoom in on an artery in a first view, which may cause a second view to zoom to the same artery. When the user focuses or zooms in on one or more arteries, the summary box 310, and other portions of the medical imaging report, may automatically update correspondingly. For example, if a user focuses on one artery, the summary box 310 may update to show the artery and sub portions such as branching arteries thereof. Additionally, the one or more views in the summary view 320 may be depicted at predetermined angulations.

Some arteries or portions thereof may have a lumen diameter that is too small to accurately image, or that is below a predetermined lumen diameter threshold. These small arteries and/or microvasculature 325 may be displayed in a different or neutral color and/or pattern, such as gray, and may be truncated after a predetermined length, a predetermined distance from the main artery, or after the lumen diameter falls below a second predetermined lumen diameter threshold.

The report summary 300 may display at least a portion of the three-dimensional model 10 or other models/meshes and/or any simulations or other results determined by solving the equations 30, such as the simulated blood pressure model 50, the simulated blood flow model 52, and/or the cFFR model 54.

The key 330 may contain symbols and/or alphanumeric text to allow a reader to interpret the medical imaging report. The small vasculature key 332 may disclose a predetermined threshold beyond which arteries may be displayed in a small vasculature color and/or pattern, as discussed above. The occlusion symbol 334 may disclose an indicator and/or symbol which may be used in the medical imaging report to indicate an occlusion. For example, a red octagon symbol may be used. The patient-specific blood flow characteristic key 336 may be depicted as a spectrum graph, and may allow a reader to interpret the coloration, patterns and/or symbols which indicate the value of a patient-specific blood flow characteristic. For example, the colors associated with various cFFR values may be indicated. A predetermined threshold, such as the predetermined threshold of functional significance, may also be indicated on the patient-specific blood flow characteristic key 336.

As discussed above, the report summary 300, or any portion of the medical imaging report, may display text, symbols, indicators, images, graphs, charts, colors, video and/or audio. Although the medical imaging report shown herein relates to a patient's heart, the medical imaging report may present results relating to any organ or blood flow system in the body.

Figure 4:
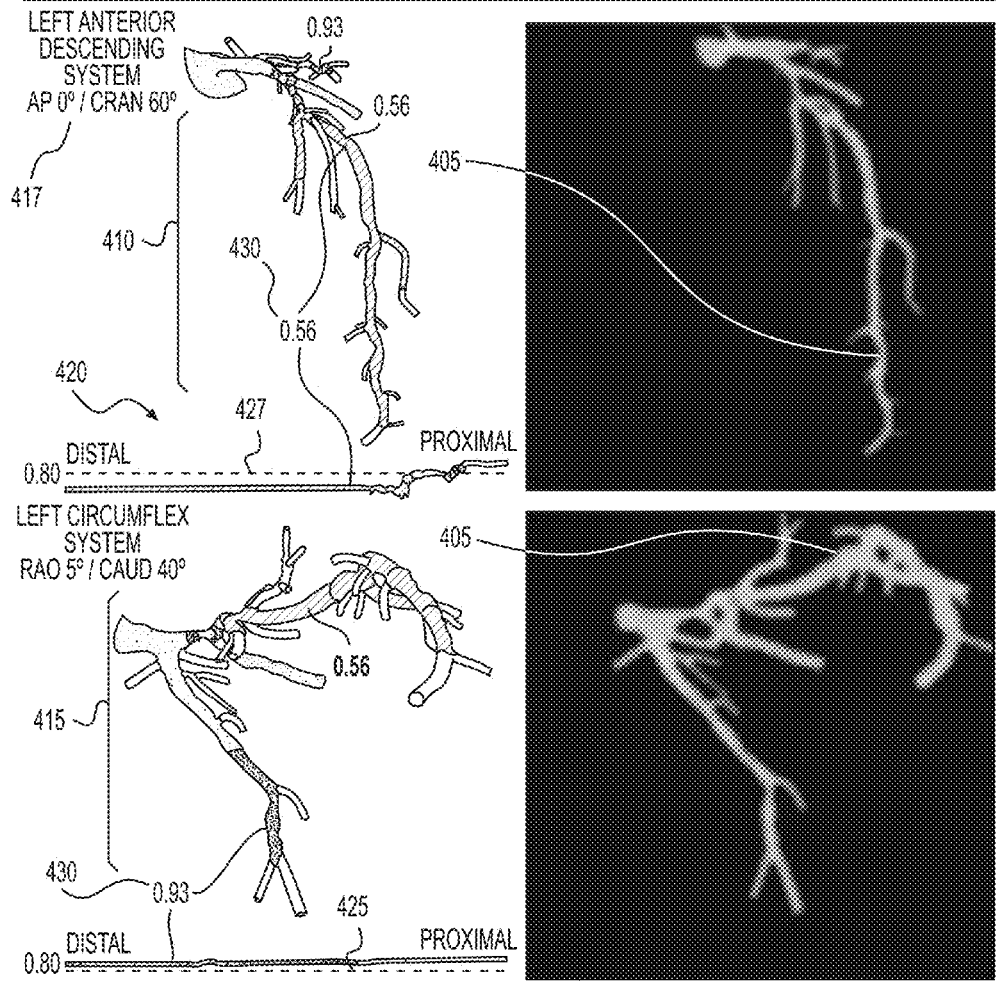
FIG. 4 shows an example artery detail that may be included in a medical imaging report.

FIG. 4 shows an example artery detail page 400. The summary header 305 may be displayed on each page of the medical imaging report, which may be identical to, or differ from, the summary header 305 on the report summary 300.

One or more arteries and/or systems listed in summary box 310 may be separately displayed on the artery detail page 400. Patient-specific anatomy images, which may be derived from a CCTA, may be automatically divided into the individual arteries and/or systems listed in summary box 310. Alternatively, a single artery and/or system listed in the summary box 310 may be divided into multiple arterial images 410, 415 for display on the artery detail page 400. One or more anatomy images 405 may be displayed proximately and corresponding to arterial images 410, 415.

Small and microvasculature may be truncated from the arterial images 410, 415 based on the lumen diameter to allow users to view the major arteries more easily.

Each arterial image 410, 415 may display an artery and/or system corresponding to those listed in the summary box 310. Each artery and/or system may be displayed with an angulation that may be modified by a user, such as by clicking and dragging the arterial image 410, 415. If a user modifies an arterial image 410, 415, the corresponding anatomy image 405 may by modified in a corresponding manner, such that the angulation of the arterial image 410, 415 and the corresponding anatomy image 405 match. The arterial images 410, 415 may also be displayed in a default angulation according to a predetermined setting. The angulation 417 may also be displayed to the user. For example, arterial image 410 may represent the LAD system. The default angulation may be anterior posterior (AP) 0 degrees, and cranial angulation (Cran) 60 degrees. The arterial image 415 may represent the LCX system. The default angulation may be right anterior oblique (RAO) 5 degrees, and caudal angulation 40 degrees. The default angulation may vary, and may be user and/or administrator configurable.

The coloration, patterning, indicators and/or visual display of the arterial images 410, 415 may correspond to that of the summary view 320. Alternatively, the coloration, patterning, indicators and/or visual display of the arterial images 410, 415 may vary from the summary view 320. For example, in the summary view 320, entire arteries may be colored a solid color corresponding to the most functionally significant cFFR therein. Alternatively, in the arterial images 410, 415, each point in the artery may be colored based upon the corresponding cFFR value at that point.

The arterial images 410, 415 may be displayed with a corresponding pullback curve 420 and 425. Each pullback curve 420, 425 may be created to represent an artery oriented substantially linearly along an axis, for example along a horizontal axis (X-axis). Each end of each pullback curve 420, 425 may represent a proximal and distal end of the artery. The thickness of each pullback curve 420, 425 line may correspond to the lumen diameter of the associated artery. A patient-specific blood flow characteristic may be represented along a second axis of the pullback curve 420 and 425. For example, the vertical axis (Y-axis) may represent cFFR values at points along the artery. A predetermined threshold 427 for a patient-specific blood flow characteristic may also be displayed. For example, the cFFR threshold for functional significance of 0.80 may be displayed as a horizontal line.

As discussed above, indicators may be placed at points along a view of one or more arteries corresponding to locations where patient-specific blood flow characteristics meet a predetermined threshold. For example, an indicator such as a pin may be placed on an artery at the point with the most functionally significant cFFR. Dual indicators 430 which indicate both the arterial images 410, 415 and the pullback curves 420, 425 may also be placed. Other dual indicators 430 which connect multiple corresponding points in two or more graphs are possible, and may be used to connect corresponding points of any graphs discussed herein, using any indicators discussed herein. For example, dual indicators 430 may connect corresponding points between an anatomy image 405 and an arterial image 410. Dual indicators 430 may have the features of any other indicators discussed herein. For example, a dual indicator 430 value which exceeds a predetermined threshold may be displayed larger and/or in bold. The color, pattern, and any other aspect of the visual depiction of the pullback curve 420, 425 may correspond to the visual depiction of the same artery in the arterial images 410 and 415. Alternatively, the visual depiction of the pullback curve 420, 425 may differ in color, pattern, and any other aspect of the visual depiction from the arterial images 410 and 415, and may be depicted in manners discussed elsewhere herein. Dual indicators 430 may also be displayed only when a predetermined patient-specific data threshold, such as cFFR functional significance, is reached. While dual indicators are discussed above, a single indicator may connect corresponding points in any number of graphs and/or images.

FIG. 5 shows an example artery detail page 500 that may comprise identical or similar features to the artery detail page 400, and may display a plurality of angulations and/or visual depictions of one or more arteries or arterial systems. Arterial images 505 and 510 may represent two different angulations of an artery and/or arterial system, in this case the RCA. Arterial image 505 displays the RCA with a left anterior oblique (LAO) angulation of 30 degrees, and a cranial angulation of 20 degrees. Arterial image 510 displays the RCA with a right anterior oblique view of 40 degrees. Depictions of the same artery and/or arterial system may vary by more than the angulation. One arterial image may focus on a portion of the artery displayed in a second arterial image. Depictions of the same artery and/or arterial system in a plurality of views may differ in color, detail, zoom, pattern displayed, indicators displayed, blood flow characteristics depicted, accompanying images and/or graphs, predetermined threshold values, lumen diameter threshold for display, and whether occlusions are depicted.

FIG. 6 depicts an example report conclusion 600 of a medical imaging report. The medical imaging report may contain a functional quality score section 605 which reports an assessment of the quality of the patient-specific anatomical data which, as discussed above, may be obtained non-invasively, e.g., by CCTA. Uncertainty in the patient-specific anatomical data may have an effect on the accuracy of calculated patient-specific blood flow characteristics, such as the cFFR (also known as FFRct) and the accuracy of the medical imaging report.

The quality of the patient-specific anatomical data for one or more arteries and/or arterial systems may be quantified and categorized into two or more quality categories based upon predetermined thresholds. The quality categories may include, for example, excellent, good, and fair. The report conclusion 600 may display the determined quality categories for each artery and/or arterial system in the medical imaging report at 605. The report conclusion may also display an interpretation of the quality categories 610, and other warnings and information 615.

FIG. 7 depicts an example report summary 700 which may display indicators of one or more arterial occlusions. If any artery and/or system has one or more arterial occlusions, this information may be placed in the summary line 705, and may be given first priority over other candidates for the summary line 705. Any arteries that contain an occlusion may be listed with an occlusion indicator 715 in the summary box 710. The occlusion indicator 715, as discussed above, may be depicted as a red octagon, although any other alphanumeric or graphical indicator may be used. Occlusion indicators may also be placed in the summary view 720 at locations corresponding to an occlusion 725. Arteries may be truncated in the summary view 720 at the point of the occlusion, or within a predetermined distance thereof.

Figure 8:
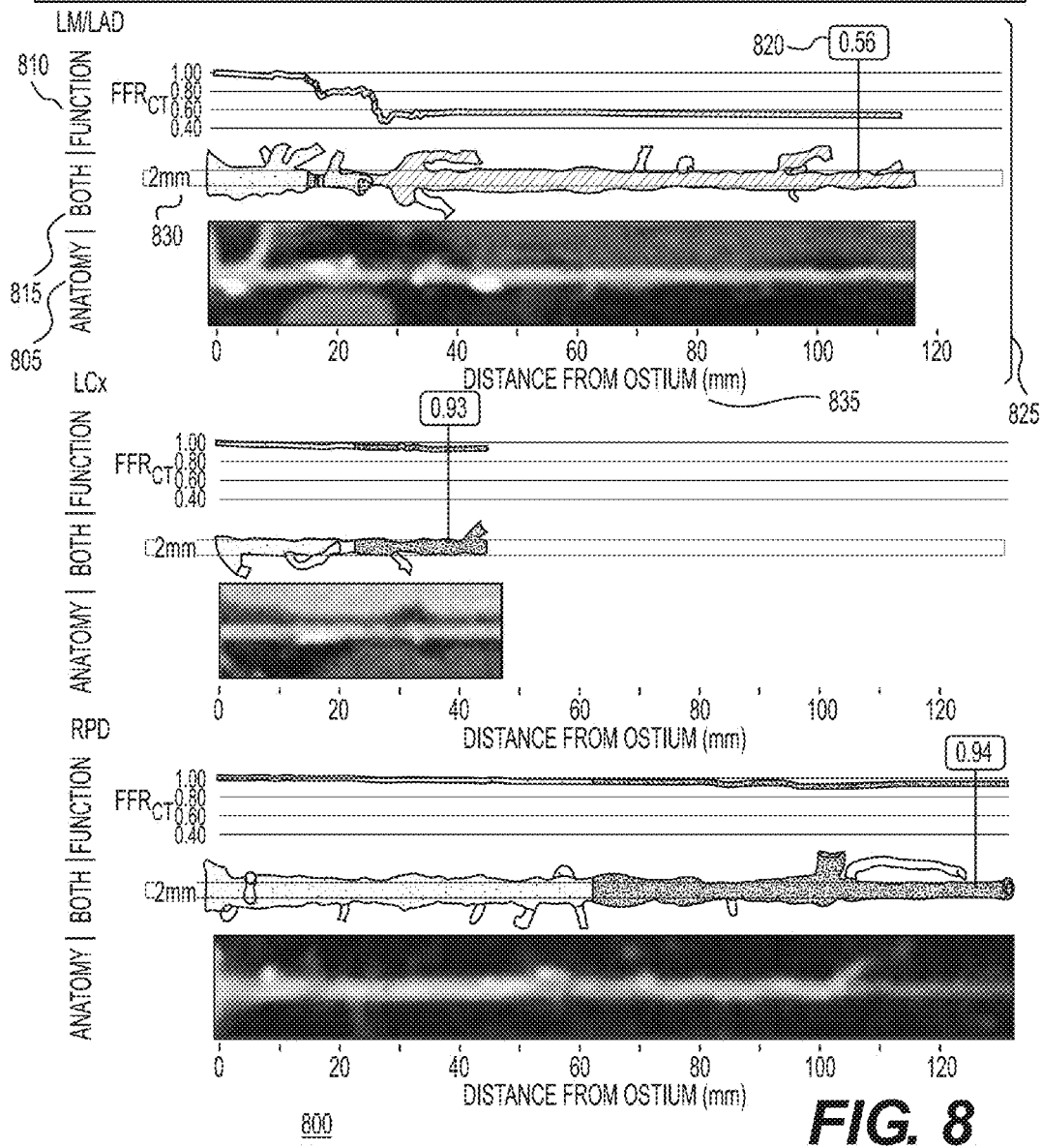
FIG. 8 depicts an example artery detail of a medical imaging report.

FIG. 8 depicts an example artery detail page 800 of a medical imaging report. An anatomy image 805 of an artery may be oriented in a substantially linear fashion. As also discussed above, patient-specific blood flow characteristics, such as cFFR, may be determined and displayed in a pullback curve 810. As discussed above, one axis of the pullback curve may represent proximal and distal portions of an artery. The pullback curve may be colored, patterned, or otherwise indicated according to one or more patient-specific blood flow characteristic values. A second axis of the pullback curve may also represent a patient-specific blood flow characteristic, such as cFFR. The combined anatomy image 815 may render a representation of the anatomical image 805 in two or three dimensions, while conveying the patient-specific blood flow characteristics of the pullback curve 810. The value of a patient-specific blood flow characteristic may represented at the corresponding point in the artery by coloring, patterning, or otherwise indicating the artery. Values determined to be important according to predetermined criteria, such as the lowest or most functionally significant cFFR 820, may also be indicated on any of the images 805, 810 and 815. A leader line may also extend across two or more of the images 805, 810 and 815 in order to indicate the value of a patient-specific blood flow characteristic. A guide to the lumen diameter may also be placed along an axis of the artery 815, and the guide may run the length of the axis. A distance from the ostium 835 may also be indicated along an axis of the artery 825. Artery 825 displays the left main and LAD arteries, although any artery may be shown such as the LCX artery, and right posterior descending (RPD) artery. Additional smaller arteries 827 that intersect along the artery 825 may automatically be truncated at the intersection point, at a predetermined distance from the intersection point, or at a predetermined distance from the artery 825.

Figure 9A:
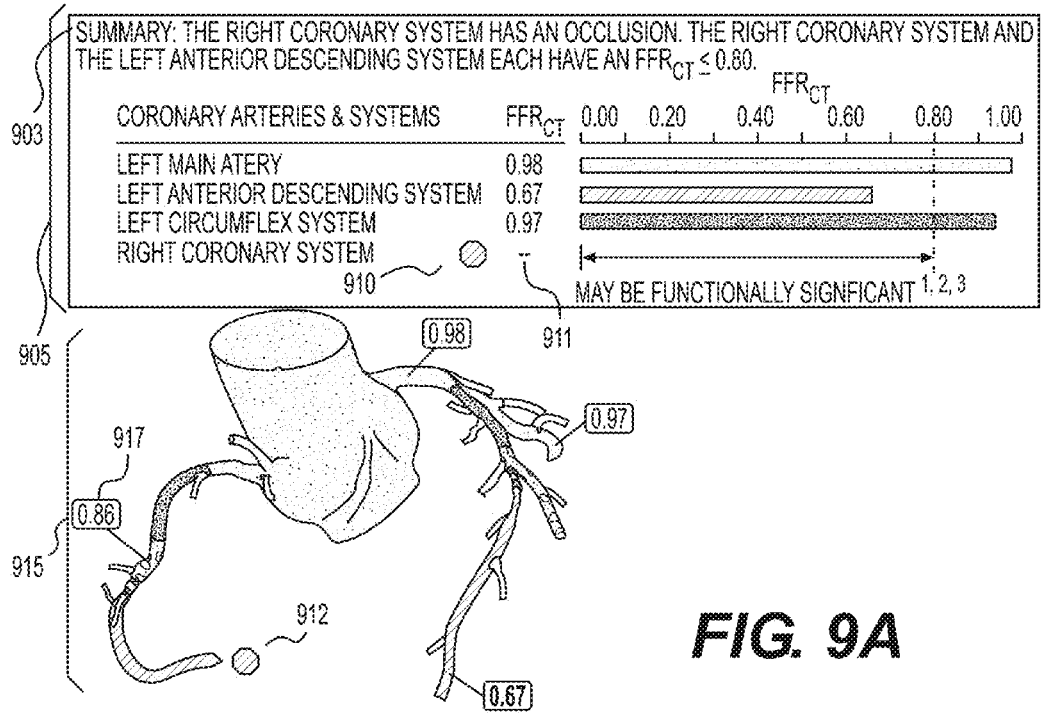
FIGS. 9A-9N depict summary views and summary boxes that may be used when one or more arteries are occluded.

FIGS. 9A-9N depict summary views and summary boxes that may be used when one or more arteries are occluded. In FIG. 9A, the RCA contains an occluded vessel. This may cause the summary table 905 to display an indicator 910 of the occlusion, and may cause one or more patient-specific blood flow characteristics in the associated artery to be incalculable, which may be indicated with a blank space, a dash or some other indicator 911. An occlusion symbol 912 may also be displayed proximate to the RCA and/or proximate to the occlusion point on the summary view 915. One or more pins 917 or other indicators conveying a cFFR value at that point, or other patient-specific blood flow characteristic, may be placed proximate to the last arterial sidebranch preceding the occlusion. If no sidebranch exists on the occluded vessel, a cFFR pin or other indicator of a patient-specific blood flow characteristic may not be placed. Occlusions in non-primary vessels with a lumen diameter above a predetermined threshold, such as above 1.8 millimeters, may cause an occlusion indicator to be placed in the summary view 915, but the indicator may not be placed in the summary table 905. Occlusions in non-primary vessels, or any vessel below a predetermined lumen diameter threshold, such as below 1.8 millimeters, may result in no occlusion indicator placement in the summary view 915 and/or the summary table 905. In the summary table 905, the occlusion indicator 910 may be placed to the left of, or otherwise proximate to, the patient-specific blood flow characteristic value, such as the cFFR 911. If multiple occlusions exist in a given artery and/or arterial system, one occlusion indicator 901 in the summary table 905 may nonetheless be displayed. Alternatively, if a plurality of occlusions exist in a given artery, text may be inserted into the summary line 903 stating that the artery has multiple occlusions.

As a rule, all occlusions of primary and/or non-primary vessels may be listed in the summary line 903. Non-primary vessels may be defined as those having below a predetermined lumen diameter threshold. Instances of occlusions may be listed in the summary line 903 first and with priority over any other summary line 903 content, such as content reporting of values of patient-specific blood flow characteristics.

Figure 9B:
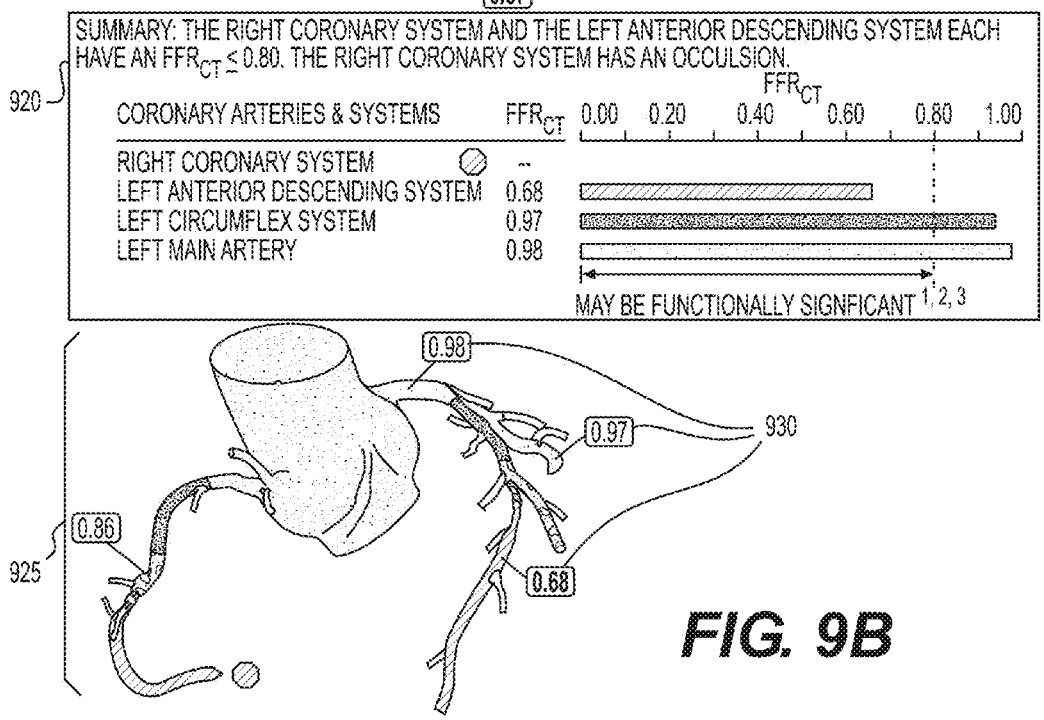

In FIG. 9B, the summary line 920 may list occlusion occurrences with a lower priority over other summary line 903 content, such as content reporting of values of patient-specific blood flow characteristics. Priority, and thereby the order of listing in the summary line 920, may be dynamically modified based upon whether the patient-specific blood flow characteristic meets a predetermined threshold, such as a cFFR value meeting a predetermined threshold of functional significance.

FIG. 9B also illustrates a plurality of pins 930, which may automatically be placed in the summary view 925. The pins may correspond to patient-specific blood flow characteristic values, such as cFFR values, as discussed above. Pins and/or other indicators may be placed automatically based on anatomical and blood flow characteristics, such as anatomical narrowings in the arteries.

FIG. 9C shows an example summary table 932 and summary view 935 that illustrate an example placement of an occlusion indicator. In the summary table 932, arteries with an occlusion may not be given priority and preferential display over arteries that do not. In the summary view 935, a pin may be placed above the first sidebranch vessel most proximal, and/or immediately upstream, to the occlusion.

FIG. 9D shows an example summary table 937 and summary view 940 that illustrate example placement of an occlusion indicator. In the summary table 937, arteries and/or arterial systems that contain at least one occlusion may be given priority such that they are listed before arteries and/or arterial systems that do not contain an occlusion.

FIGS. 9E and 9F show example indicators of one or more occlusions in a sidebranch of a primary artery. In such a case, the summary table 941 may still display an occlusion indicator with the associated primary artery. In the summary view 942, rather than displaying the occlusion indicator at the end of the primary artery, the occlusion indicator 912 may be displayed proximate to the sidebranch artery that has the occlusion. FIG. 9F displays a summary table 945, which may prioritize the listing of the primary artery containing the occlusion, even though the occlusion is in a sidebranch of the primary artery.

FIGS. 9G and 9H depict an example indicator of an occlusion in a vessel that does not contain sidebranches. As discussed above, an indicator may be placed of the value of a patient-specific blood flow characteristic at a sidebranch vessel proximate to the occlusion. In the summary views 947, artery 948 does not contain a sidebranch vessel, so an indicator of the patient-specific blood flow characteristic may not be placed. In the summary table 949 of FIG. 9H, the artery containing an occlusion but lacking sidebranch arteries prior to the occlusion may be given priority in the listing of arteries and/or arterial systems.

FIGS. 9L and 9J depict summary views 950 and 951, which contain occlusions in non-primary vessels and/or vessels with a lumen diameter below a predetermined threshold. For example, occlusions 952 and 953 may be detected, but it may be determined that the associated arteries have a lumen diameter below a predetermined threshold of 1.8 millimeters, so occlusion indicators may not be placed in summary views 950 and 951, or in summary tables 954 and 955. FIG. 9J also illustrates a summary table 955 in which arteries and/or arterial systems may be ordered by an associated patient-specific blood flow characteristic, such as the most functionally significant cFFR value.

FIGS. 9K and 9L depict summary tables 956 and 957, along with summary views 958 and 959, which display multiple arteries and/or arterial systems that contain occlusions. Summary views 958 and 959 depict an occlusion of a primary artery 960, wherein an indicator of the occlusion may be placed at the terminal end of the primary artery display. Summary views 958 and 959 also depict an occlusion of a non-primary artery 962, wherein an indicator of the occlusion may be placed at the terminal end of the non-primary artery display. FIG. 9L also depicts a summary table 957 in which primary arteries and/or arterial systems contain an occlusion, even if the occlusion is located in a sidebranch artery, may be given priority in the listing over arteries that do not contain an occlusion.

FIGS. 9M and 9N depict summary tables 965 and 967, and summary views 969 and 970 which depict multiple occlusions in a single artery and/or arterial system. An occlusion indicator 972 may be placed proximate to a primary artery that is determined to contain an occlusion. An indicator 974, such as a pin indicating a patient-specific blood flow characteristic, may be placed upstream and/or above the first sidebranch artery proximal to the occlusion. Additional occlusion indicators 976 may also be placed proximate to any sidebranch arteries that are determined to contain an occlusion. The summary line 978 in the summary box 967 may contain text or other indication that a given artery has a plurality of occlusions.

Any of the images shown in FIGS. 9A-9N may be generated using patient-specific data 10, physiological laws 20, and equations of blood flow 30. Any of the images shown in FIGS. 9A-9N may be further generated using computer 40, and may be displayed at any location in one or more medical imaging reports, an example of which is shown in FIGS. 3-6.

Figure 10:
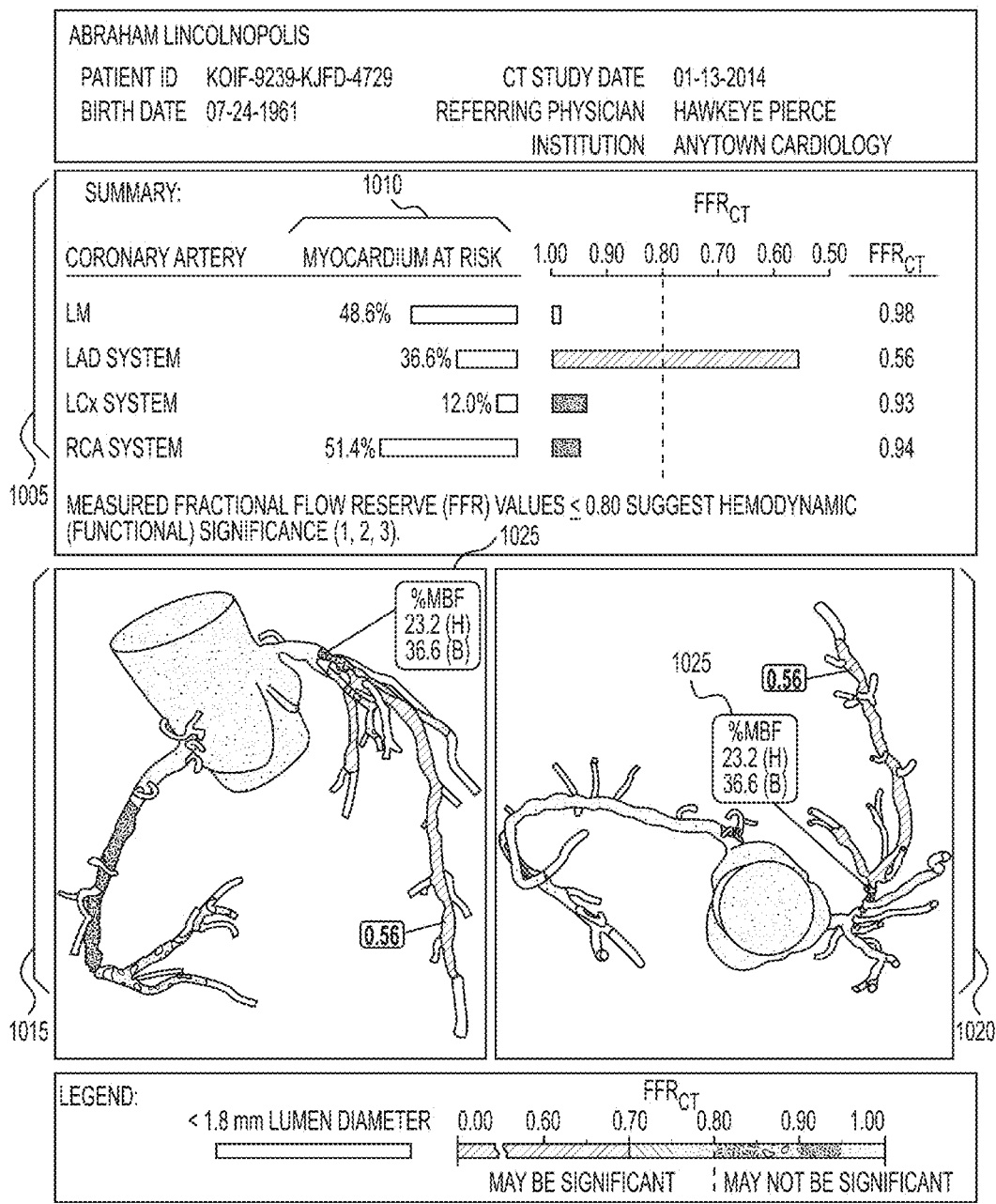
FIG. 10 shows an example report summary of a medical imaging report.

FIG. 10 shows an example report summary 1000 of a medical imaging report. Summary table 1005 may contain a listing of arteries and/or arterial systems and the associated percentage of the myocardium that would placed at risk by an ischemia in each artery and/or arterial system. For example, 48.6% of the myocardium may receive blood either directly or indirectly from the LM artery while the patient is in a baseline physiological state. The myocardium at risk (MAR) percentage for a given point in an artery may change depending on the physiological state of the patient. The percentages listed in the MAR section 1010 may correspond to the percentage of the myocardium affected by the associated point in an artery at baseline by default, although percentages may also be displayed corresponding to a patient in a state of hyperemia, or any other physiological state. The physiological state corresponding to the values displayed may be user-configurable. In summary views 1015 and 1020, the MAR percentage may be displayed, in an indicator 1025, at a given point in an artery and/or arterial system. Upon a determination that a patient-specific blood flow characteristic, such as cFFR, meets a predetermined threshold, the indicator 1025 and/or MAR section 1010 may be displayed. For example, if a cFFR value is determined to be below a 0.80 threshold of functional significance for a point in an artery, the indicator 1025 displaying the percentage of myocardium at risk may be displayed proximate to the artery. The MAR may also be displayed corresponding to arteries that contain an occlusion.

FIG. 11A shows an example report summary 1100 of a medical imaging report that displays a stent 1105. The stent 1105 may be displayed as one or more indicators along an artery at a location corresponding to an actual or possible stent in a patient. If there is an occlusion in the artery with an associated stent indicator, at least a portion of the artery may be grayed out and/or otherwise marked to indicate a lack of patient-specific blood flow data. The artery may also be grayed out and/or otherwise marked because, due to the presence of a stent, no clinical validation exists for the cFFR results, and therefore results cannot be communicated back to the clinician. The summary box 1110 may also lack patient-specific blood flow data in the instance of an occlusion. If there is no occlusion in the artery, patient-specific blood flow data may be indicated on or proximate to the artery, as discussed elsewhere herein.

If the placement of a stent is being simulated, after a stent is placed, patient-specific blood flow data may be estimated based upon the stent 1105 location, as shown in FIG. 11B. The estimation may be performed by, in part, updating the three-dimensional model 10. Estimated patient-specific blood flow data, such as cFFR, may be displayed at one or more points in the medical imaging report. The user may interact with the graphical user interface in order to place and move the stent 1105, which may cause an estimation of patient-specific blood flow data based upon the stent 1105 location and/or relocation. Stent placements may also be automatically suggested by evaluating one or more patient-specific blood flow values and/or one or more models discussed herein, and indicating the suggestion on the display. If more than one candidate stent location would cause an improvement in patient-specific blood flow values for given locations in one or more arteries, one candidate stent location may be selected for recommendation to the user based upon the degree of improvement in patient-specific blood flow values. For example, if two candidate stent locations in an artery both cause the value of cFFR at a location in the artery to increase above a predetermined threshold, the location which In this manner, physicians and/or patients may evaluate various stent location and treatment options.

Any of the images shown in FIGS. 11A-11B may be generated using patient-specific data 10, physiological laws 20, and equations of blood flow 30. Any of the images shown in FIGS. 11A-11B may be further generated using computer 40, and may be displayed at any location in one or more medical imaging reports, an example of which is shown in FIGS. 3-6.

FIGS. 12A-12HH illustrate example graphs and other interface elements that may be displayed in a summary box 310 or other portion of a medical imaging report.

Figure 12A:
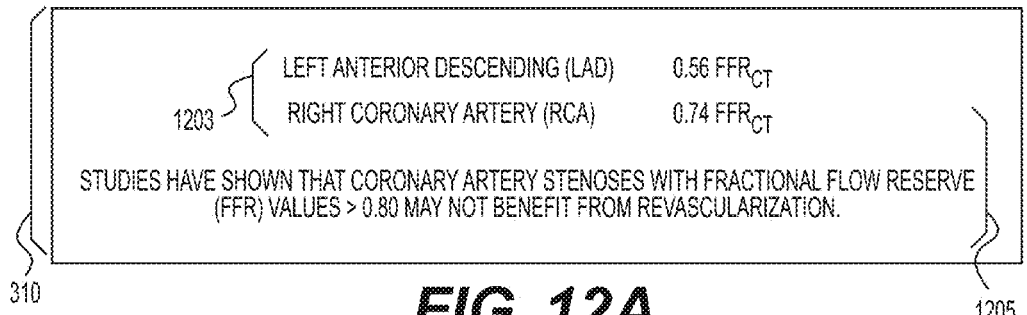
FIGS. 12A-12HH illustrate example graphs and other interface elements that may be displayed in a summary box or other portion of a medical imaging report.

FIG. 12A displays a list of arteries and/or arterial systems 1203 that may be displayed in summary box 310. Healthy arteries that meet one or more predetermined thresholds may automatically be excluded from the list of arteries 1203. The summary box 310 may also have language explaining patient-specific blood flow data values 1205, such as predetermined threshold values and/or values that are to be considered functionally significant.

Figure 12B:
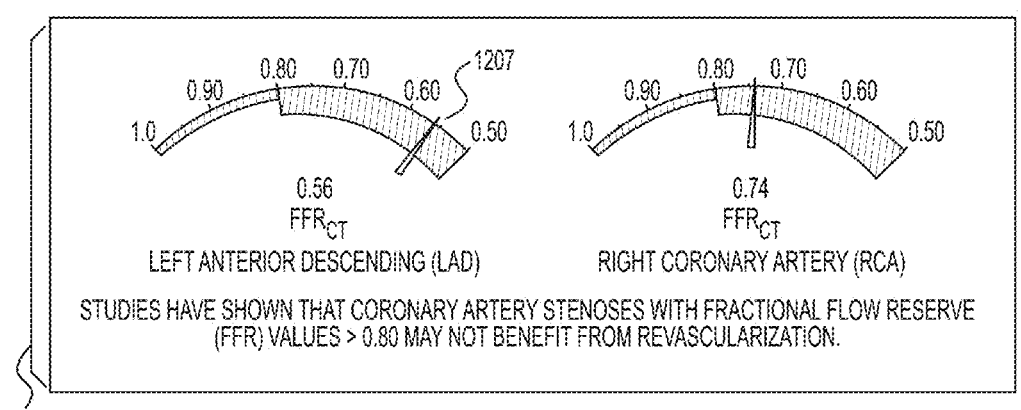

FIG. 12B displays an example speedometer-style graph that may be displayed in the summary box 310. The value of one or more patient-specific blood flow characteristics, such as cFFR, may be indicated with a needle 1207. The needle moving to the right, which would indicate a higher and more dangerous speed in an automobile, may indicate a patient-specific blood flow characteristic value, such as cFFR, that is more functionally significant and/or poses greater health risks for the patient.

Figure 12C:
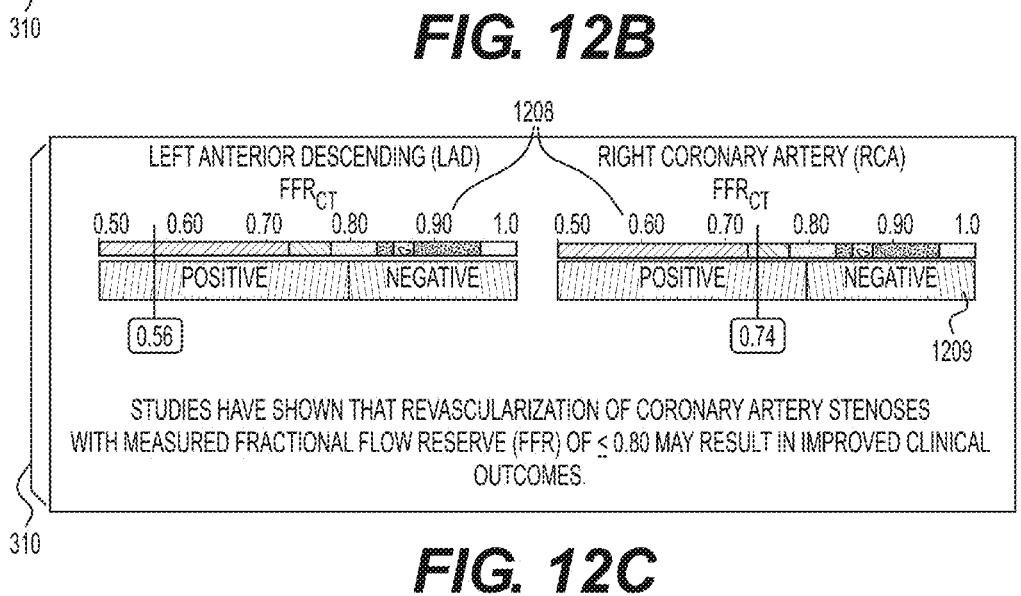

FIG. 12C displays one or more example horizontally-oriented spectrum graphs 1208 displaying one or more patient-specific blood flow characteristic values. A predetermined threshold of functional significance 1209 may be displayed on the graph as positive and negative, for example. The spectrum graph 1208 may be depicted as a color spectrum, pattern spectrum, alphanumeric spectrum, or other series of indicators that convey the value of the patient-specific blood flow characteristic to the user.

Figure 12D:
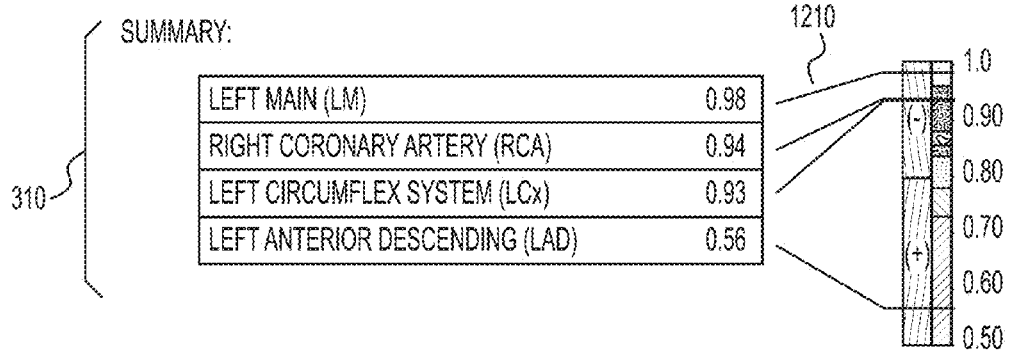

FIG. 12D displays one or more example spectrum graphs, which may also be known as column graphs, displaying one or more patient-specific blood flow characteristic values, such as cFFR, which may be displayed in a vertically-oriented manner. One or more arteries may be displayed in the summary box 310 and may have indicators such as lines and/or arrows 1210 pointing from each artery to a corresponding patient-specific blood flow characteristic value. The one or more arteries in the summary box 310 may be sorted by most functionally significant cFFR, or sorted by the values of some other patient-specific blood flow characteristic.

Figure 12E:
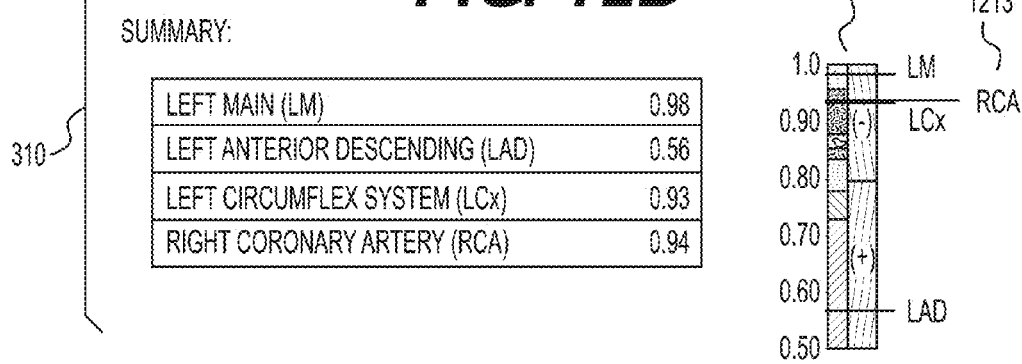

FIG. 12E displays one or more example spectrum graphs 1215 displaying one or more patient-specific blood flow characteristic values, such as cFFR. Each artery may have a corresponding abbreviation 1213 that may be displayed along with a corresponding indicator at the spectrum graph 1215.

Figure 12F:
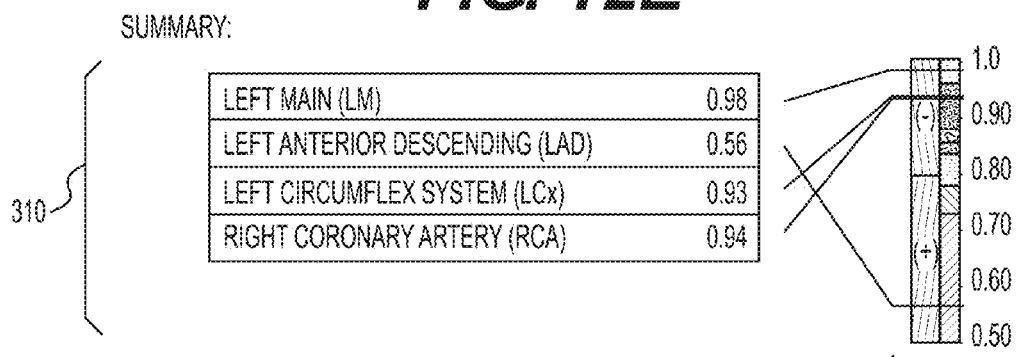

FIG. 12F displays one or more example spectrum graphs displaying one or more patient-specific blood flow characteristic values. The listed arteries in the summary box 310 may be unsorted, or may be sorted by artery name, artery abbreviation, or other sorting technique.

Figure 12G:
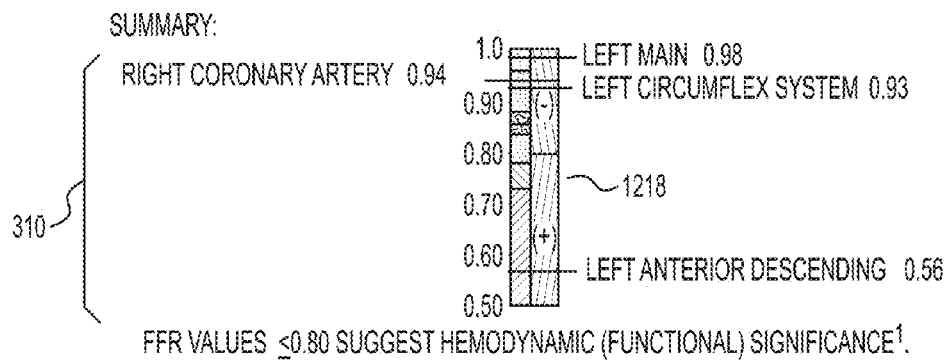

FIG. 12G is an example vertically-oriented spectrum graph 1218 displaying one or more patient-specific blood flow characteristic values for one or more arteries. The names of each artery may be indicated proximate to the corresponding patient-specific blood flow characteristic value on the spectrum graph 1218. Each value in the spectrum graph 1218 may correspond to a patient-specific blood flow characteristic value in each artery that may have the greatest effect on the patient's health, such as the most functionally significant cFFR value in the corresponding artery.

Figure 12H:
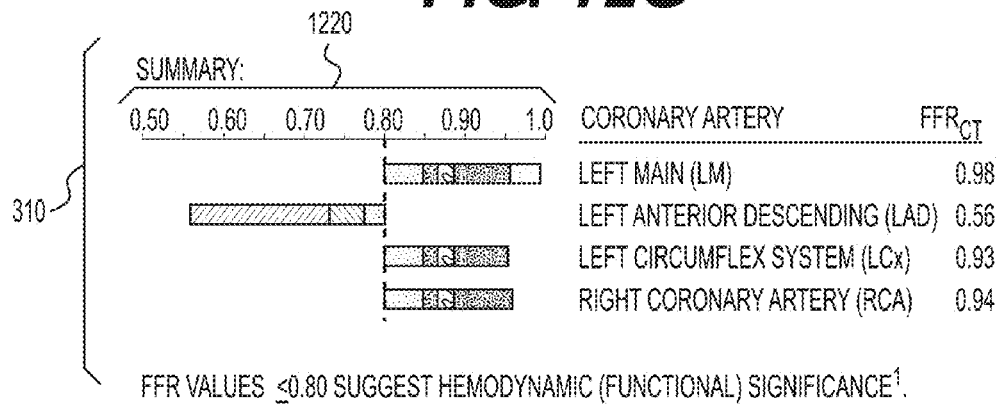

FIG. 12H shows an example bar graph 1220 in which patient-specific blood flow data values may be displayed as bars extending from a predetermined threshold. The predetermined threshold may be a threshold of functional significance of cFFR, or any other predetermined threshold associated with patient-specific blood flow data. Each bar in the bar graph may display a plurality of colors, patterns and/or other indicator(s) associated with the value of a patient-specific blood flow at the corresponding point on the bar.

Figure 12I:
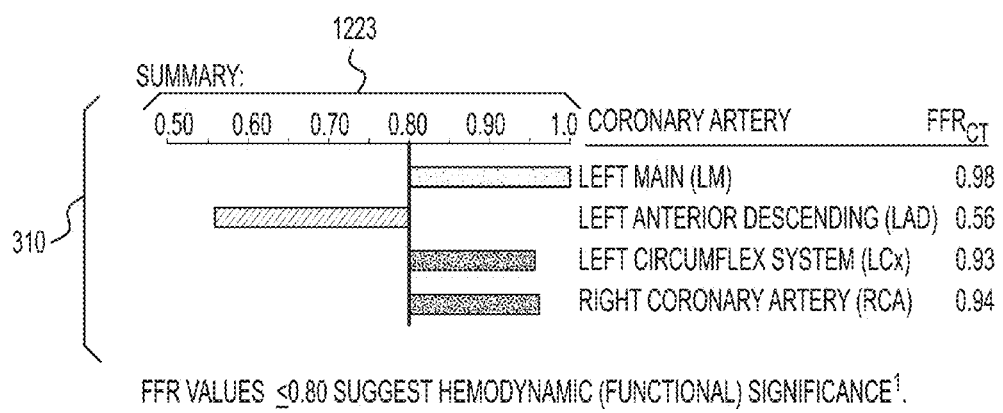

FIG. 12I shows an example bar graph 1223 in which patient-specific blood flow data values may be displayed as bars extending from a predetermined threshold. Each bar in the bar graph may also display a single color, pattern, and/or indicator(s) associated with a value of the patient-specific blood flow data that may have the greatest effect on the patient's health. For example, the most functionally significant (lowest) value of cFFR in each artery may determine the size of each bar in the bar graph, as well as the color, pattern, and/or other indicator(s) associated with each bar.

Figure 12J:
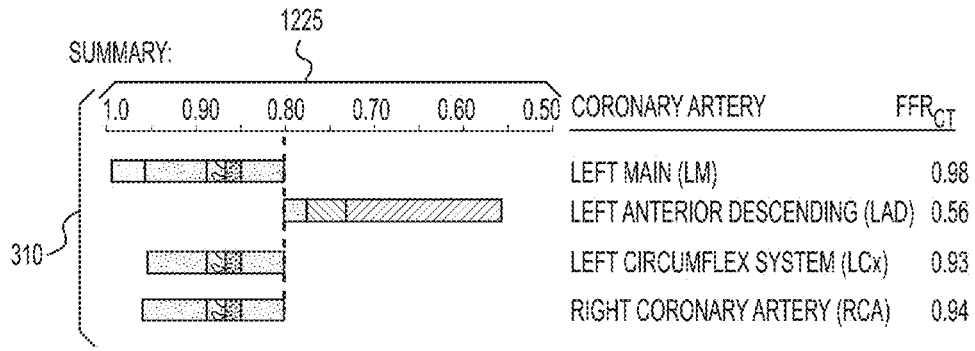

FIG. 12J shows an example bar graph 1225 in which the axis for patient-specific blood flow data values may run with the opposite orientation to the direction of the example in FIG. 12H.

Figure 12K:
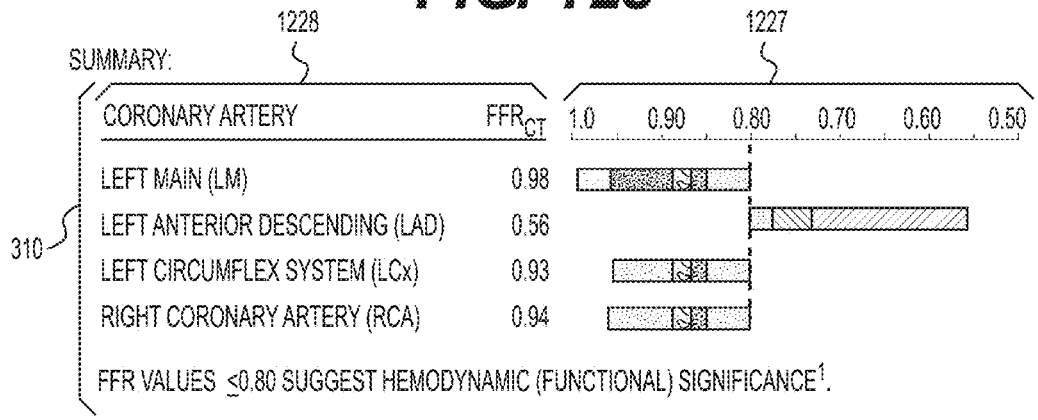

FIG. 12K is an example showing that the layout of the example summary box 310 may vary. For example, bar graph 1227 may be placed to the right of the corresponding list of one or more arteries and/or arterial systems 1228.

Figure 12L:
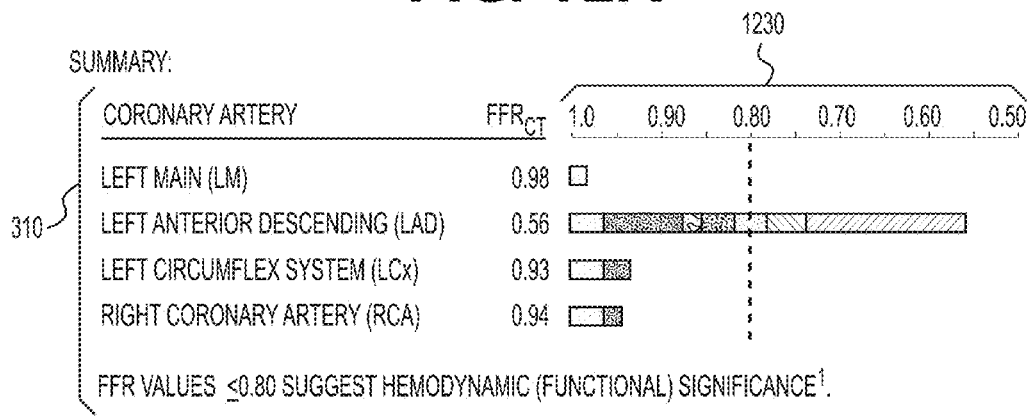

FIG. 12L displays an example bar graph 1230 in which patient-specific blood flow data values may be displayed as bar extending from the maximum value down to the actual value. Each bar in the bar graph may display a plurality of colors, patterns and/or other indicator(s) associated with the value of a patient-specific blood flow at the corresponding point on the bar.

Figure 12M:
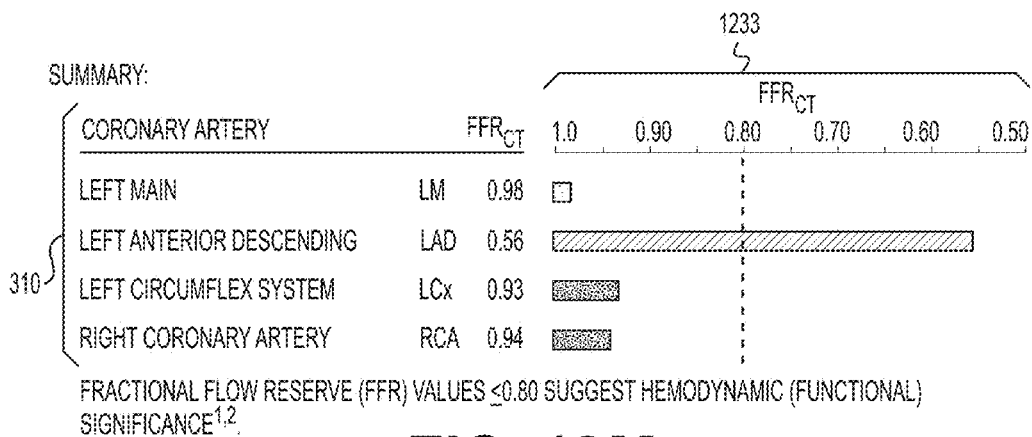

FIG. 12M displays an example bar graph 1233 in which patient-specific blood flow data values may be displayed as bar extending from the maximum value down to the actual value. Each bar in the bar graph may also display a single color, pattern, and/or indicator(s) associated with a value of the patient-specific blood flow data that may have the greatest effect on the patient's health. For example, the most functionally significant (lowest) value of cFFR in each artery may determine the size of each bar in the bar graph, as well as the color, pattern, and/or other indicator(s) associated with each bar.

Figure 12N:
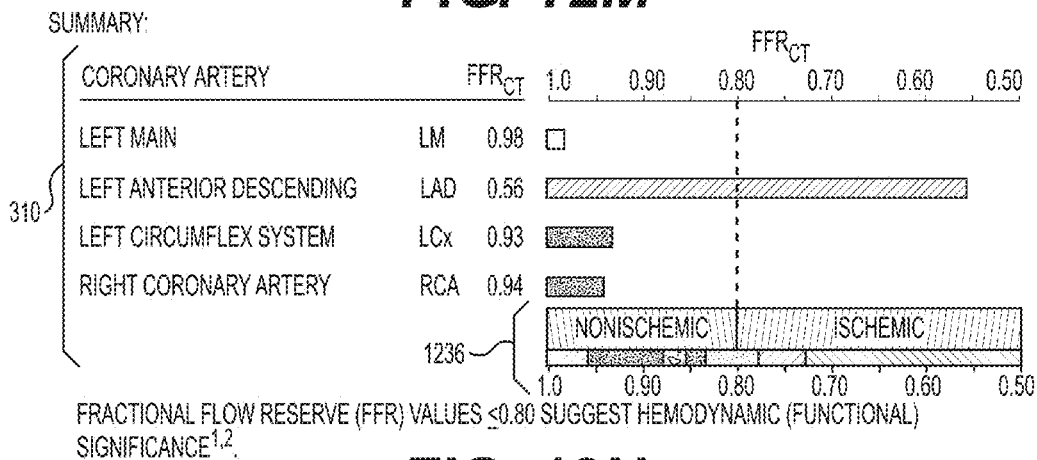

FIG. 12N displays an example summary box 310 in which patient-specific blood flow values may be displayed. The patient-specific blood flow characteristic key 1236 may allow a reader to interpret the coloration, patterns and/or symbols that indicate the value of a patient-specific blood flow characteristic. For example, the colors associated with various cFFR values may be indicated. A predetermined threshold, such as the predetermined threshold of functional significance whereupon an artery may be associated with an ischemia, may also be indicated on the patient-specific blood flow characteristic key 1236.

Figure 12O:
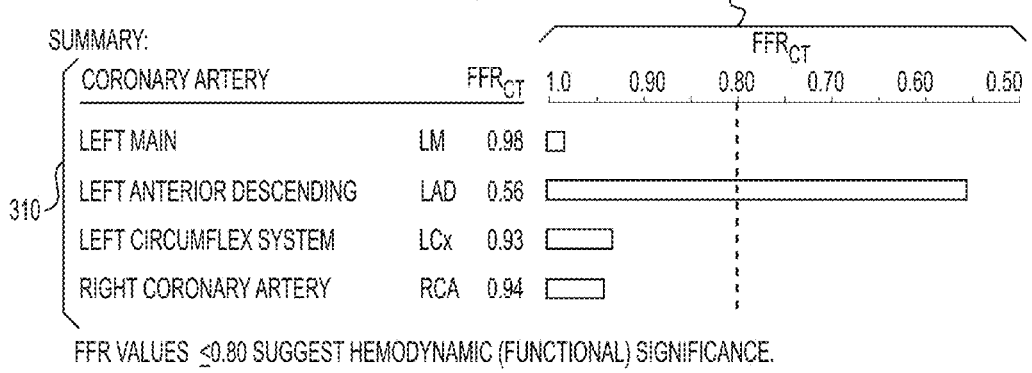

FIG. 12O displays an example summary box 310 in which patient-specific blood flow values may be displayed. Colors of the bar graph 1238 may be rendered in black and/or grayscale to allow colorblind users and users with black and white printers to correctly and easily interpret the bar graph 1238.

Figure 12P:
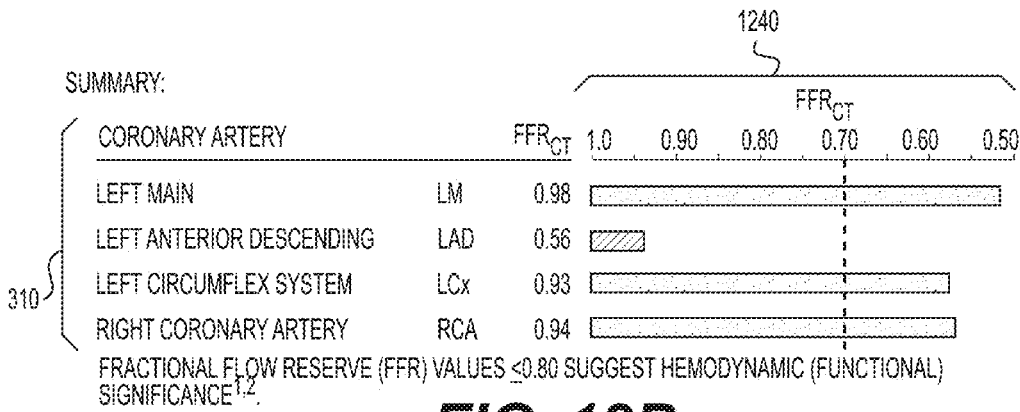

FIG. 12P displays an example summary box 310 similar to that of FIG. 12M, except that the orientation of the axis of the bar graph 1240 may be inverted. In general, in techniques presented herein, axis orientations may vary.

Figure 12Q:
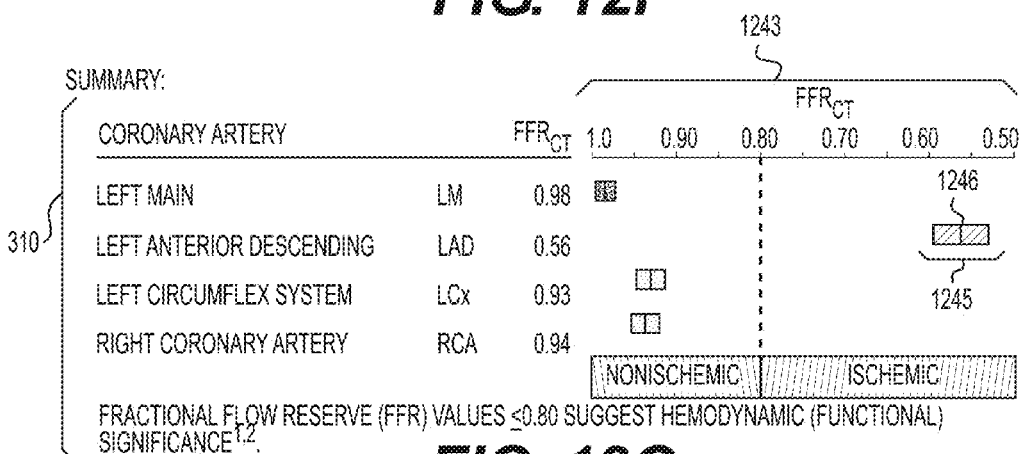

FIG. 12Q displays an example summary box 310 in which ranges of patient-specific blood flow values may be displayed in a bar graph 1243. Patient-specific blood flow data values for each artery may be associated with an uncertainty range and/or confidence interval 1245. Upon determining an uncertainty range 1245 associated with each artery, the uncertainty range 1245 values may be displayed at the corresponding point in the bar graph 1243. Each uncertainty range 1245 may be colored, patterned, given symbols and/or indicated according to a determined most likely patient-specific blood flow data value 1246. The most likely patient-specific blood flow data value 1246 may be determined according to the mean, median, or mode of patient-specific blood flow data values in an uncertainty range 1245, or peak of an uncertainty distribution curve. The most likely patient-specific blood flow data value 1246 may be displayed on the bar graph 1243.

Figure 12R:
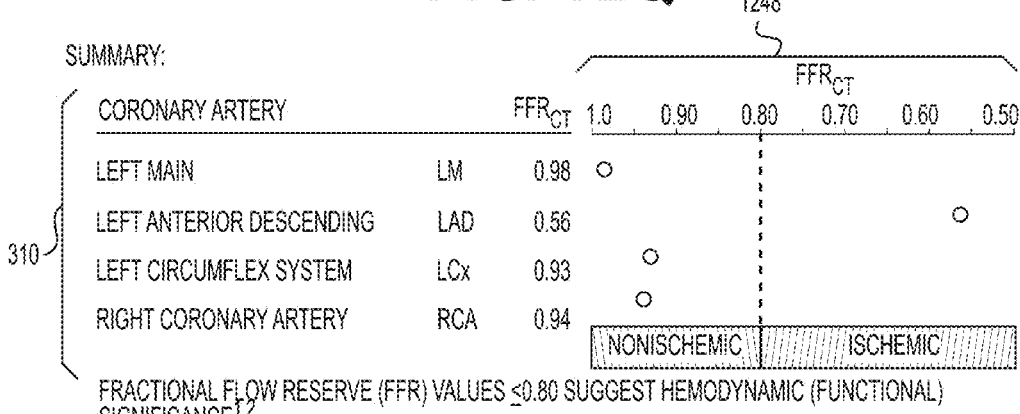

FIG. 12R displays an example summary box 310 in which the most likely patient-specific blood flow values may be displayed as points on a graph 1248. As discussed above, the most likely patient-specific blood flow data value 1246 may be determined according to the mean, median, or mode of patient-specific blood flow data values in an uncertainty range, or peak of an uncertainty distribution curve.

Figure 12S:
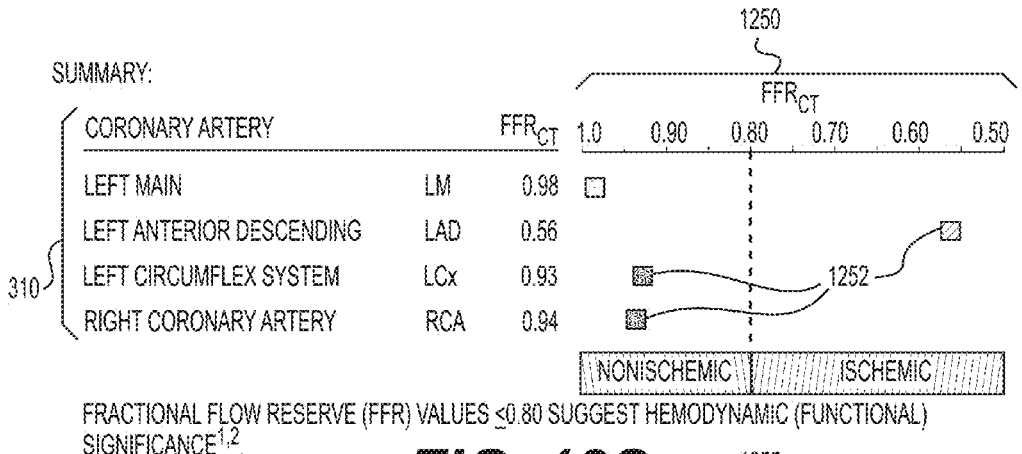

FIG. 12S displays an example summary box 310 in which patient-specific blood flow values may be displayed with indicators such as points or boxes which are colored, patterned, or otherwise indicated to correspond to a value determined to most affect the diagnosis and treatment of the patient. For example, indicators 1252 may correspond to the most functionally significant cFFR value for an artery.

Figure 12T:
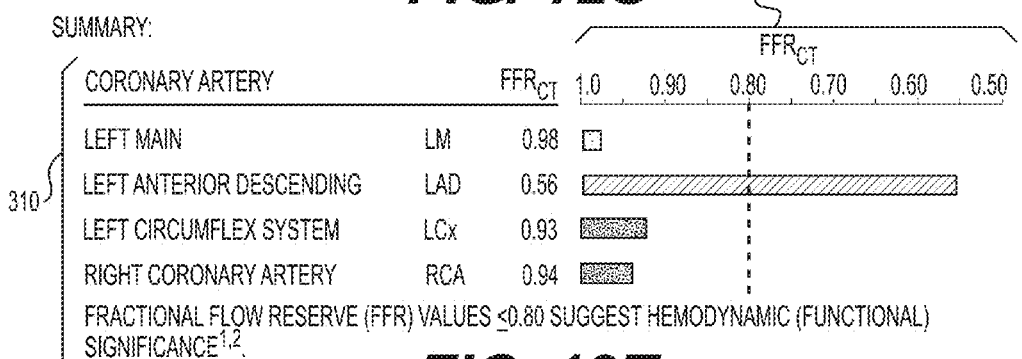

FIG. 12T displays an example bar graph 1255 in which patient-specific blood flow data values may be displayed as bar extending from the maximum value down to the actual determined value. Each bar in the bar graph may also display a single color, pattern, and/or indicator(s) associated with a value of the patient-specific blood flow data that may have the greatest effect on the patient's diagnosis and treatment. For example, the most functionally significant (lowest) value of cFFR in each artery may determine the size of each bar in the bar graph, as well as the color, pattern, and/or other indicator(s) associated with each bar.

Figure 12U:
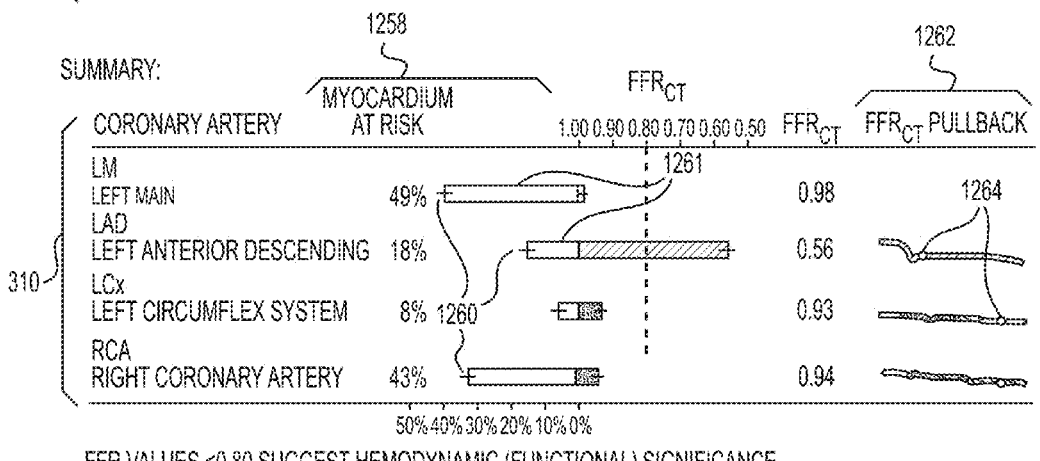

FIG. 12U displays an example summary box 310 in which a plurality of patient-specific blood flow data values may be displayed. As discussed above regarding FIG. 10, the percentage of myocardium at risk (MAR) may be displayed in the summary box 310. An indicator of a range of uncertainty 1260 of the MAR percentage may also be displayed over or proximate to each bar 1261 corresponding to the MAR value. Patient-specific blood flow data graphs may also abut and/or be displayed proximate to one or more other patient-specific blood flow graphs. For example, for a given artery, a bar corresponding to the MAR value may adjoin a bar corresponding to the most functionally significant cFFR value. One or more pullback curves or sparklines 1262 may also be displayed associated with one or more arteries and representing a patient-specific blood flow characteristic, such as cFFR. The ends of the pullback curve may represent a proximal and distal end of an artery. Patient-specific blood flow values that most affect the diagnosis and treatment of the patient may be indicated on the pullback curve. For example, the most functionally significant cFFR value may be indicated by one or more points 1264.

Figure 12V:
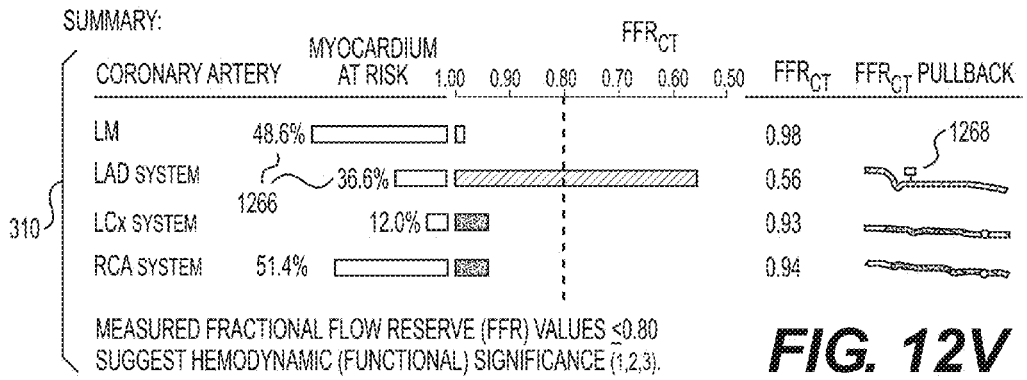

FIG. 12V displays an example summary box 310 in which a plurality of patient-specific blood flow data values may be displayed. MAR values may be displayed, as discussed above, and numerical values 1266 may be displayed at the ends of each corresponding bar. The appearance of indicators 1268 may also be modified or enhanced when an associated patient-specific blood flow data value exceeds a predetermined threshold.

Figure 12W:
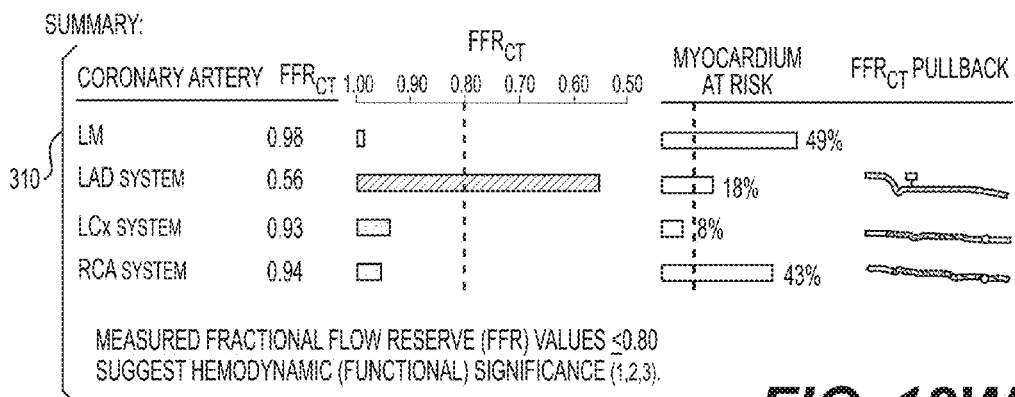

FIG. 12W also displays an example summary box 310 that illustrates that the location of the display graphs may vary, and the axis orientation of each graph may vary.

Figure 12X:
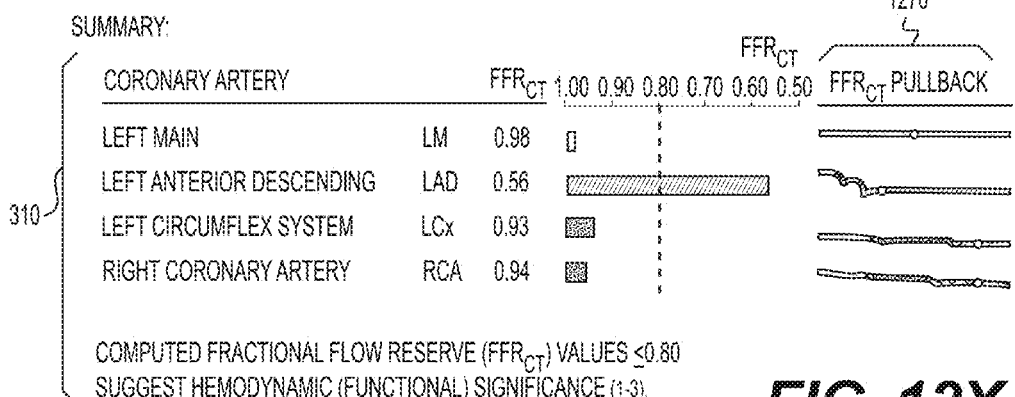

FIG. 12X displays an example summary box 310 displaying one or more pullback curves 1270. Each pullback curve represents an artery, and may be colored, patterned, or otherwise indicated at each point corresponding to an associated patient-specific blood flow data value at each point in the artery. One or more patient-specific blood flow characteristic values, such as cFFR, may be displayed in the summary box 310, and correspondingly represented at the point of inspection with a dot or other indicator on one or more pullback curves 1270.

Figure 12Y:
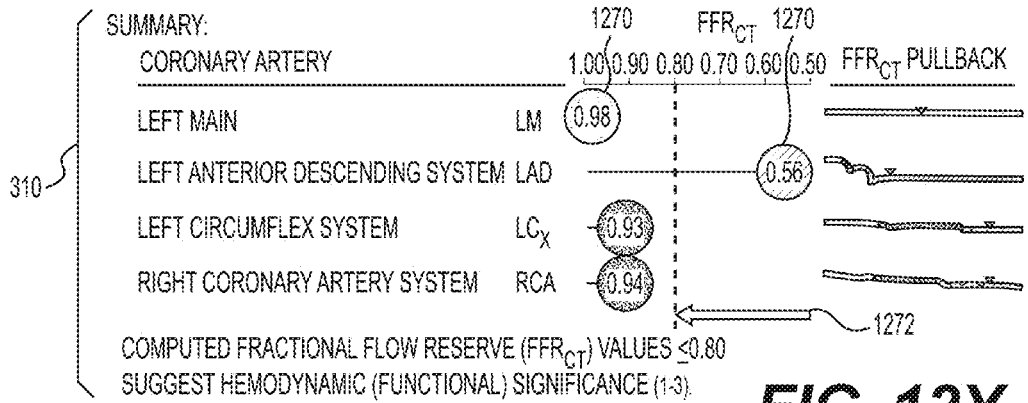

FIG. 12Y displays an example summary box 310 in which patient-specific blood flow data values may be displayed on each line or bar in the patient-specific blood flow data graph. The colors, patterns and/or appearance of the indicators 1270 may also correspond to the displayed data values. An indicator such as an arrow 1272 may also be displayed to indicate a predetermined patient-specific blood flow threshold.

Figure 12Z:
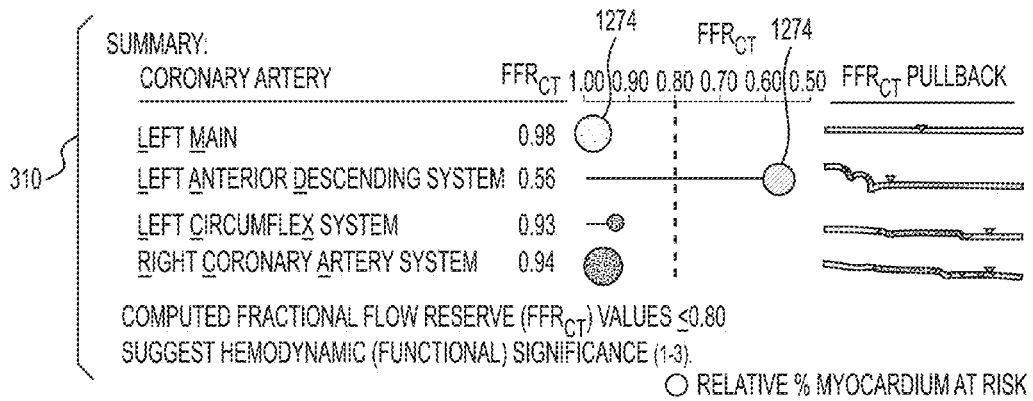
Figure 12A:
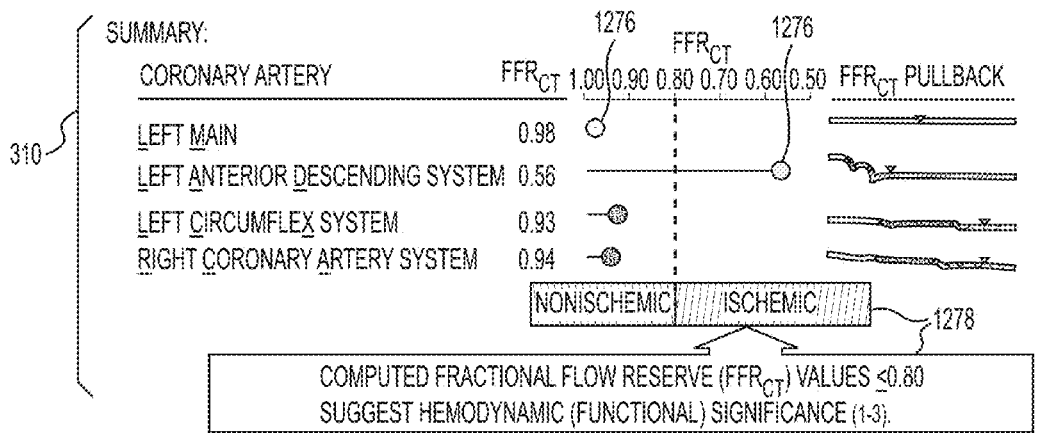
Figure 12B:
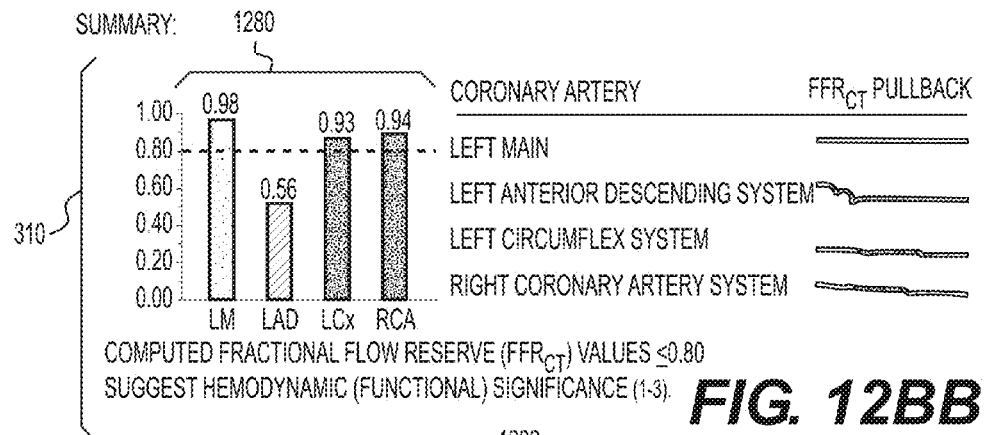
Figure 12C:
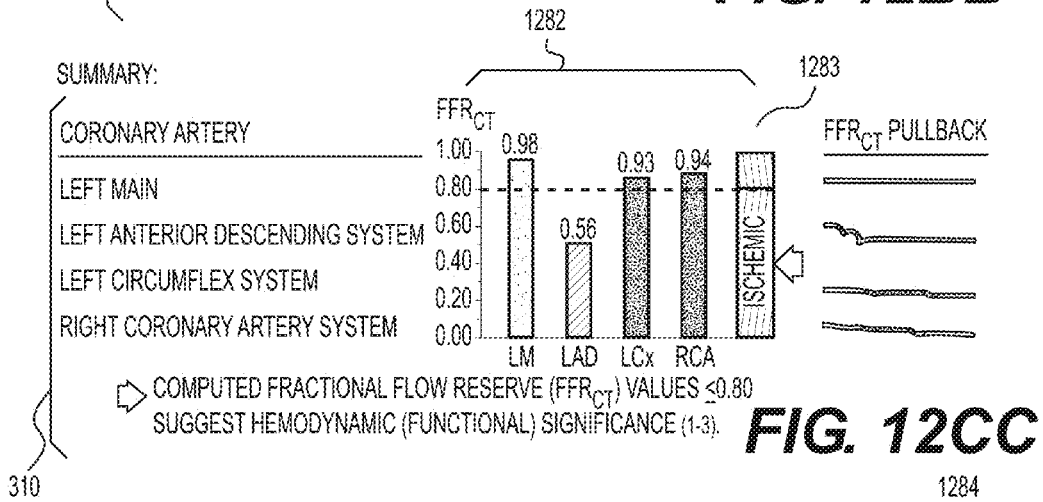
Figure 12D:
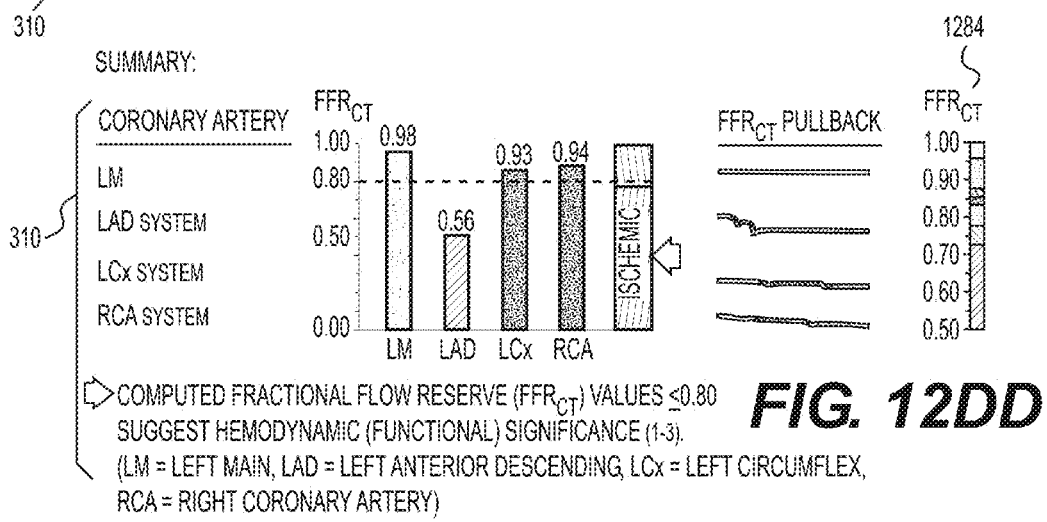
Figure 12E:
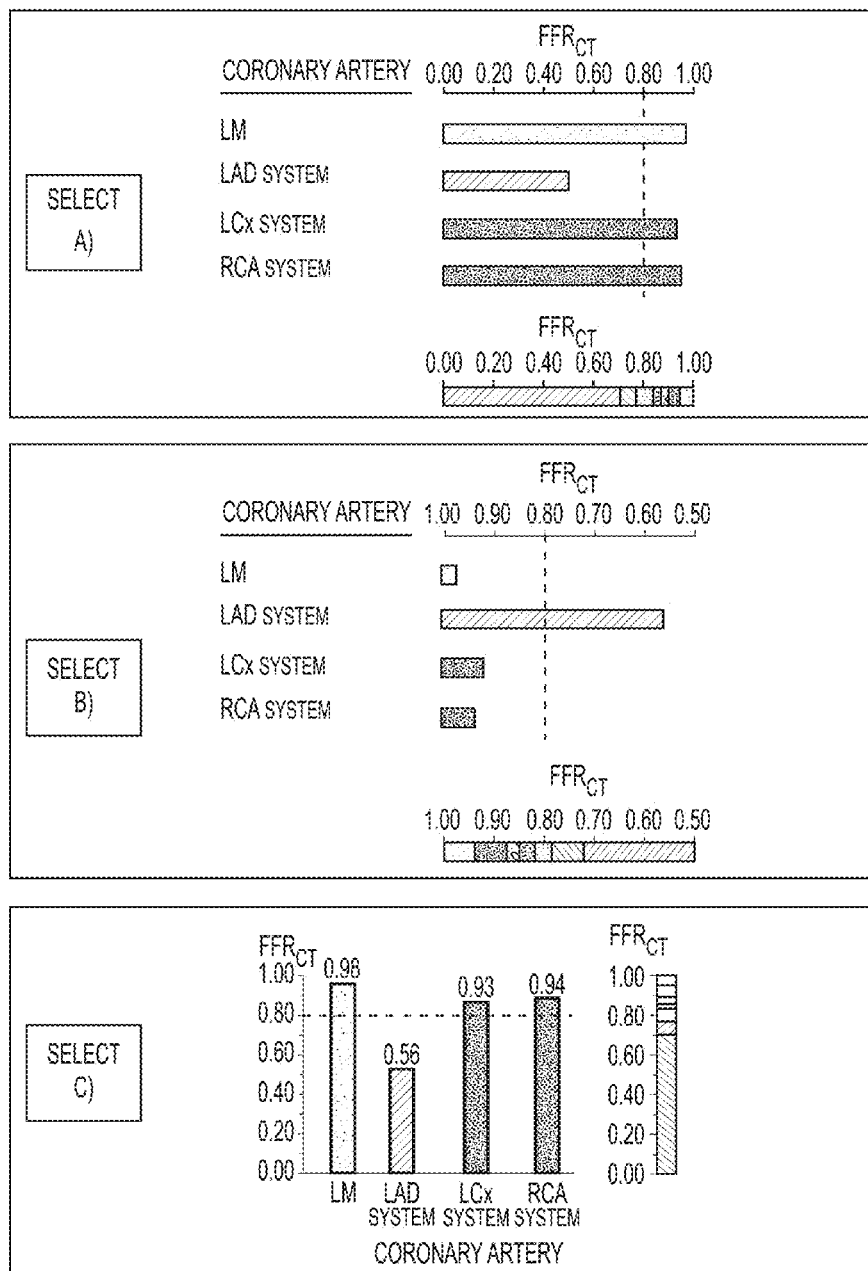
Figure 12F:
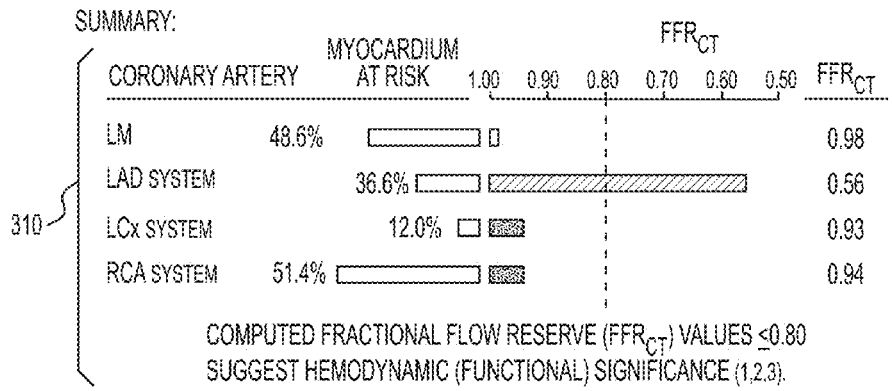
Figure 12G:
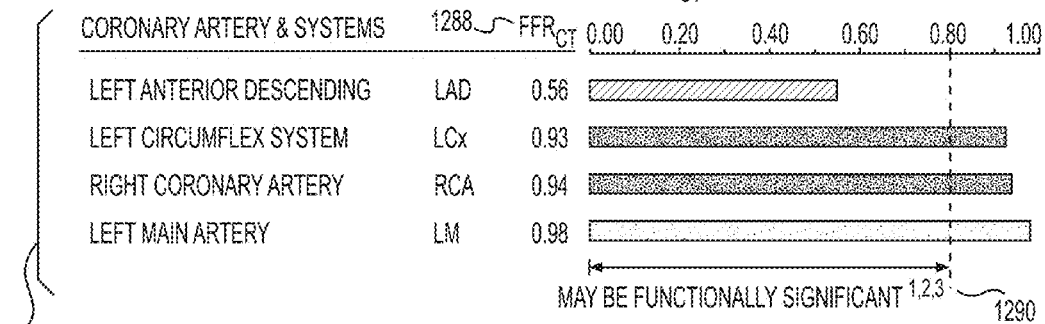
Figure 12H:
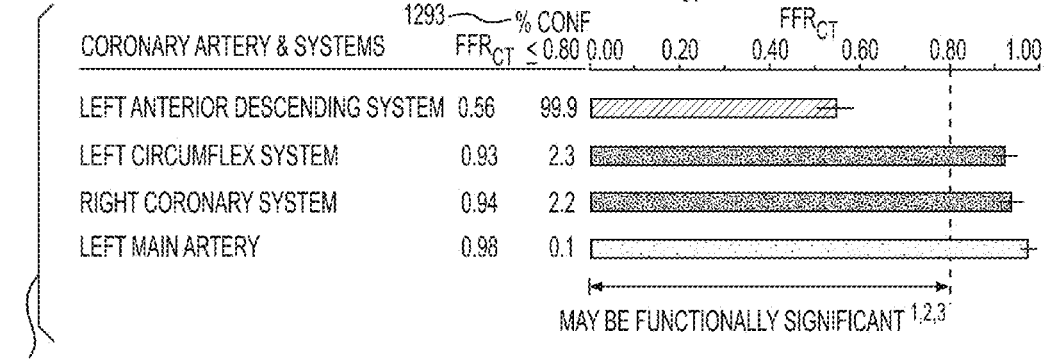

FIG. 12Z displays an example summary box 310 in which the size of indicators 1274 on a graph of a first patient-specific blood flow variable correspond to the value of a second patient-specific blood flow variable. For example, on a graph of cFFR values for a given artery, the size of one or more graph indicators 1274 may correspond to the relative MAR percentage.

FIG. 12AA displays an example summary box 310 in which the display and the placement of indicators 1276 correspond to a value of a patient-specific blood flow data variable. For example, the color and the location along the axis of indicators 1276 may both correspond to the value of the most functionally significant cFFR in each artery. An explanation 1278 of a predetermined patient-specific blood flow variable threshold may also be displayed.

FIG. 12BB displays an example summary box 310 in which a patient-specific blood flow variable may be graphed for one or more arteries in a vertical bar graph 1280. The appearance and the height of each bar in the bar graph 1280 may correspond to the value of the patient-specific blood flow variable.

FIG. 12CC displays an example summary box 310 in which a patient-specific blood flow may be graphed in a vertical bar graph 1282. An additional bar 1283 in the bar graph may be colored, patterned, or otherwise indicated to convey a predetermined threshold.

FIG. 12DD displays an example summary box 310 in which a vertically-oriented spectrum graph 1284 may be displayed, which may contain features of any of the spectrum graphs discussed herein.

FIG. 12EE displays an example user interface 1286 that may be presented so that the user may choose the summary box 310 layout. The user interface 1286 may present a plurality of summary box 310 layouts which may contain any of the graph variants discussed herein. The user may make a selection, and the appearance of summary box 310 may be set according to this selection.

FIG. 12FF displays an example summary box 310 similar to that of FIG. 12V, and illustrates that the particular graphs such as pullback curves, bar graphs, line graphs, etc. displayed in the summary box 310 may vary.

FIG. 12GG displays an example summary box 310 similar to that of FIG. 12M, and illustrates that arteries and/or arterial systems listed may be sorted by patient-specific blood flow values 1288. An indicator 1290 of a range of values that meet a predetermined threshold may also be displayed adjacent to a graph.

FIG. 12HH displays an example summary box 310 that displays a confidence that a patient-specific blood flow value meets a predetermined threshold. For example, a confidence column 1293 may display a percentage likelihood that a most functionally significant cFFR value in at least one artery is less than or equal to the predetermined functionally-significant threshold of 0.80.

While the examples discussed above show different ways elements of a summary box 310 may be displayed, the elements depicted may also be used in any combination. Any of the images shown in FIGS. 12A-12HH may be generated using patient-specific data 10, physiological laws 20, and equations of blood flow 30. Any of the images shown in FIGS. 12A-12HH may be further generated using computer 40, and may be displayed at any location in one or more medical imaging reports, an example of which is shown in FIGS. 3-6.

Figure 13A:
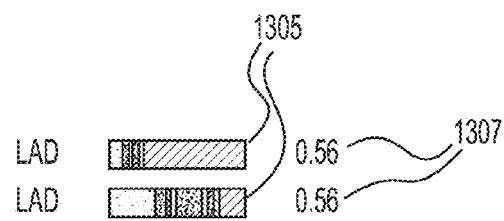
FIGS. 13A-13K illustrate example representations of arteries and/or graphs associated with patient-specific blood flow characteristics.

FIG. 13A illustrates one or more example bars 1305, also known as spark bars, displaying patient-specific blood flow values for one or more arteries as colors, patterns, or other indicators. Each end of a bar 1305 may represent a proximate and distal end of a corresponding artery. Patient-specific blood flow values 1307 may also be displayed proximate to each corresponding bar 1305.

Figure 13B:
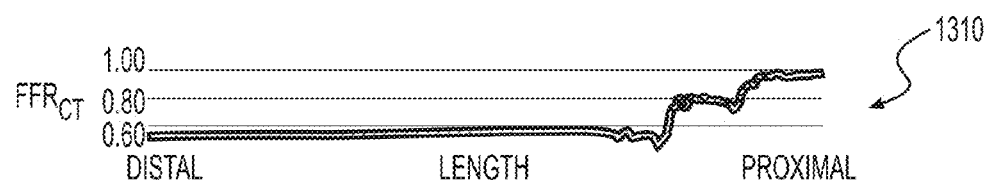

FIG. 13B illustrates a pullback curve 1310 which may be displayed proximate to and corresponding to other graphs and/or displays presented herein.

Figure 13C:
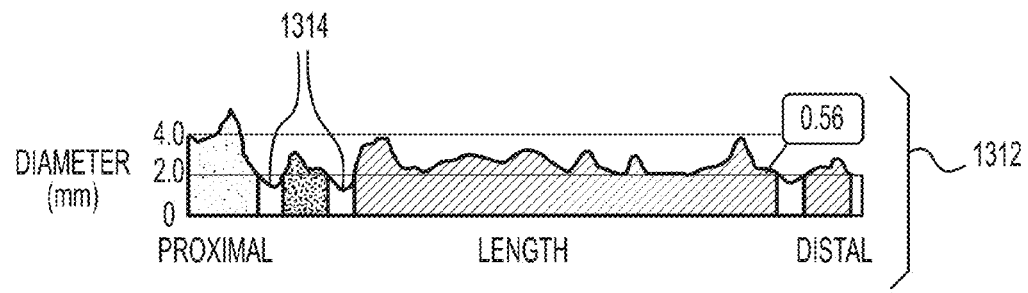

FIG. 13C illustrates an example line graph 1312 which may be displayed in the medical imaging report, wherein each end of the line graph 1312 along a first axis corresponds to a proximal and distal portion of an artery. A second axis may represent the diameter of the arterial lumen. The area underneath the line graph 1312 may be colored, patterned, or otherwise indicated according to a patient-specific blood flow value at the corresponding portion of the artery. Portions of the artery having a lumen diameter beneath a predetermined threshold 1314 may be given a neutral color and/or pattern such as gray, rather than being indicated according to a patient-specific blood flow variable.

Figure 13D:
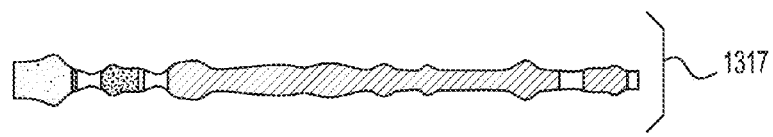

FIG. 13D illustrates an example line graph 1317 which may be bilaterally symmetrical. Each end of a first axis may correspond to a proximal and distal portion of an artery. A second axis may correspond to the lumen diameter of an artery, and line values along the first axis may be displayed in a bilaterally symmetrical manner to illustrate the lumen diameter at each corresponding point of the artery.

Figure 13E:
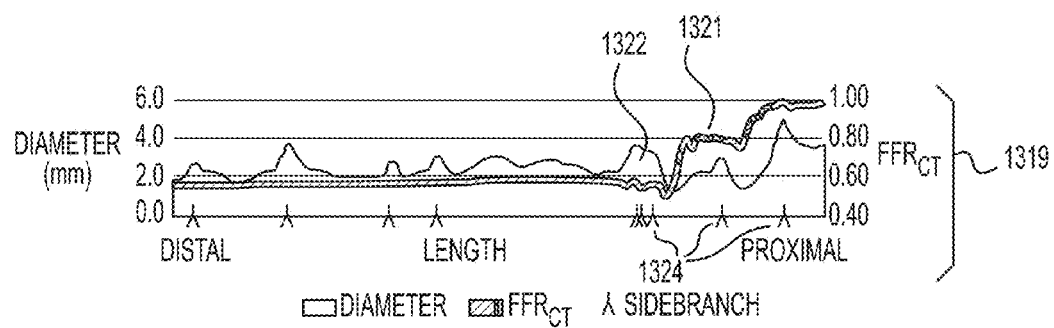

FIG. 13E illustrates an example overlay of a plurality of graphs 1319 that share common axes, wherein each graph represents a characteristic of a given artery. For example, a first graph may be a pullback curve 1321 representing cFFR values at corresponding locations of the artery. A second graph may represent the lumen diameter 1322 at corresponding locations of the artery. Each graph may share the artery characteristic represented by an axis, or two graphs may represent different artery characteristics along the same axis. For example, the pullback curve 1321 and lumen diameter graph 1322 may share the representation of the horizontal axis as signifying position or length along an artery. These two graphs may also have a differing representation of the vertical axis, with one associating the axis with lumen diameter, and the other with cFFR value. Other patient-specific characteristics may be represented in graph 1319 which may only utilize one axis, such as arterial sidebranch or artery intersection indicators 1324.

Figure 13F:
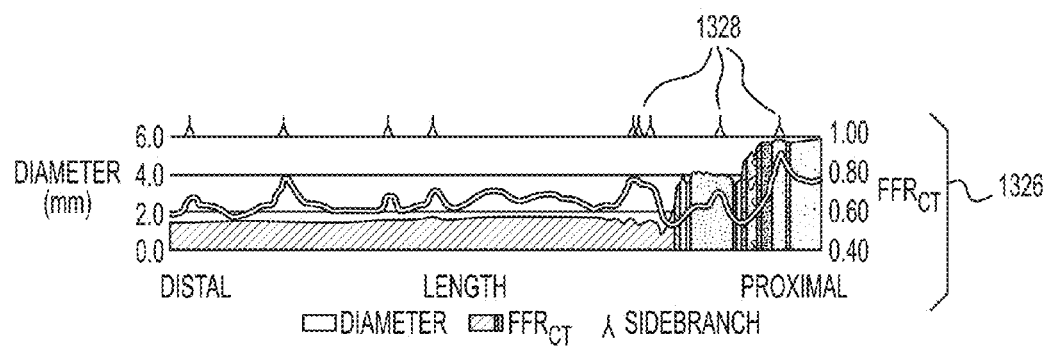

FIG. 13F illustrates an example plurality of graphs 1326 that are similar in display to FIG. 13E. The display of each graph may vary. For example, each graph may be illustrated as a line, or may be colored, patterned, or otherwise indicated between the graph line and the horizontal axis. Other patient-specific characteristics utilizing only one axis, such as sidebranch indicators 1328, may be located at the top, bottom, or at any point in the graphs 1326.

Figure 13G:
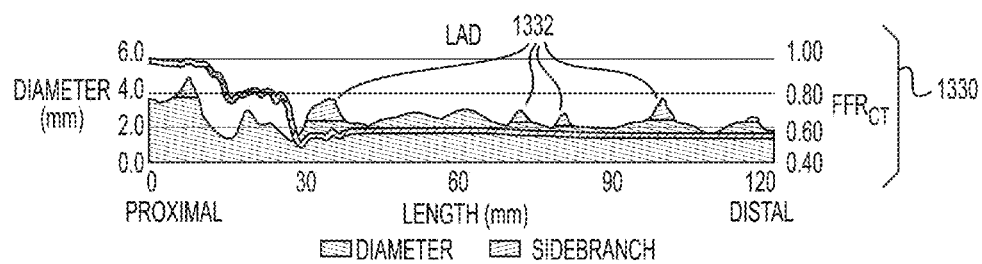

FIG. 13G illustrates an example plurality of superimposed graphs 1330 that are similar in display to FIG. 13E. Additionally, the graph associated with the lumen diameter may also be colored, patterned, or otherwise indicated to show the portion of an increase in arterial diameter that is due to the intersection of the artery represented by graphs 1330 with another sidebranch artery.

Figure 13H:
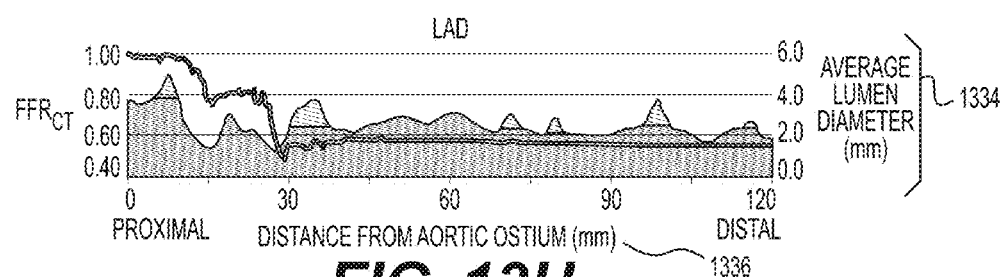

FIG. 13H illustrates an example plurality of superimposed graphs 1334 similar in display to FIG. 13G. Alternatively, one of the axes may be associated with the distance from the aortic ostium 1336. The axis label locations, graph coloring and patterning, and graph line thickness may vary.

Figure 13I:
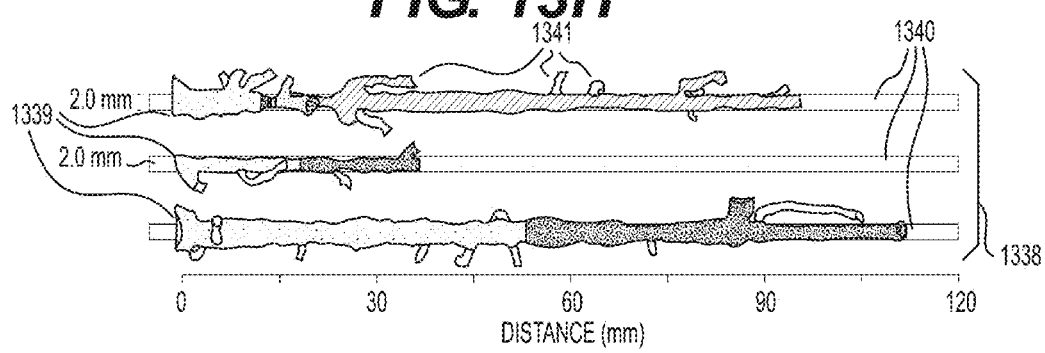

FIG. 13I illustrates one or more example arteries and/or arterial systems 1339 oriented linearly along an axis. The axis may represent the distance from the aortic ostium, for example. Each artery may be colored, patterned and/or indicated according to a patient-specific blood flow characteristic, as discussed above. A minimum arterial lumen diameter may also be indicated by a bar 1340 or other indicator displayed proximate to each artery. One or more sidebranch arteries 1341 may be displayed along each artery for a predetermined distance from the arterial intersection and/or a predetermined distance from the center of the main artery.

Figure 13J:
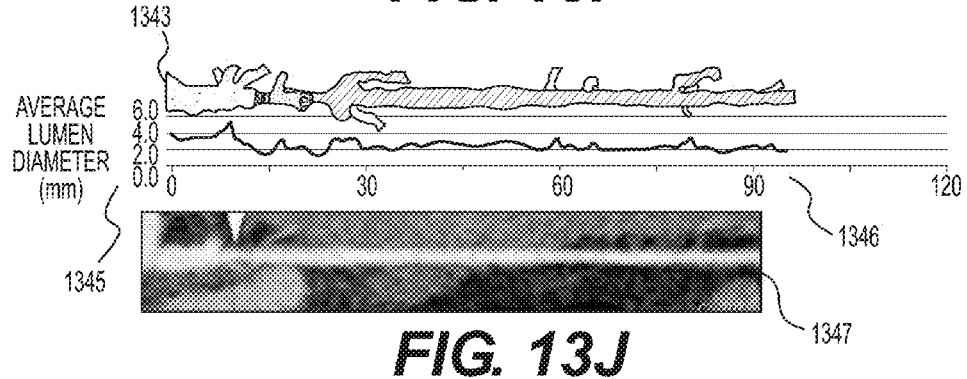

FIG. 13J illustrates one or more example arteries and/or arterial systems 1343 oriented linearly along an axis in a similar manner as FIG. 13I. A graph 1345 corresponding to a patient-specific arterial characteristic may be displayed proximate to the artery 1343. The graph 1345 may share an axis 1346 with the artery 1343. The graph 1345 may represent the average lumen diameter, for example, and the shared axis may represent the distance from the ostium. An anatomy image of the artery 1347 may also be displayed proximate to the artery 1343 and graph 1345, and may share the axis 1346, and representation thereof.

Figure 13K:
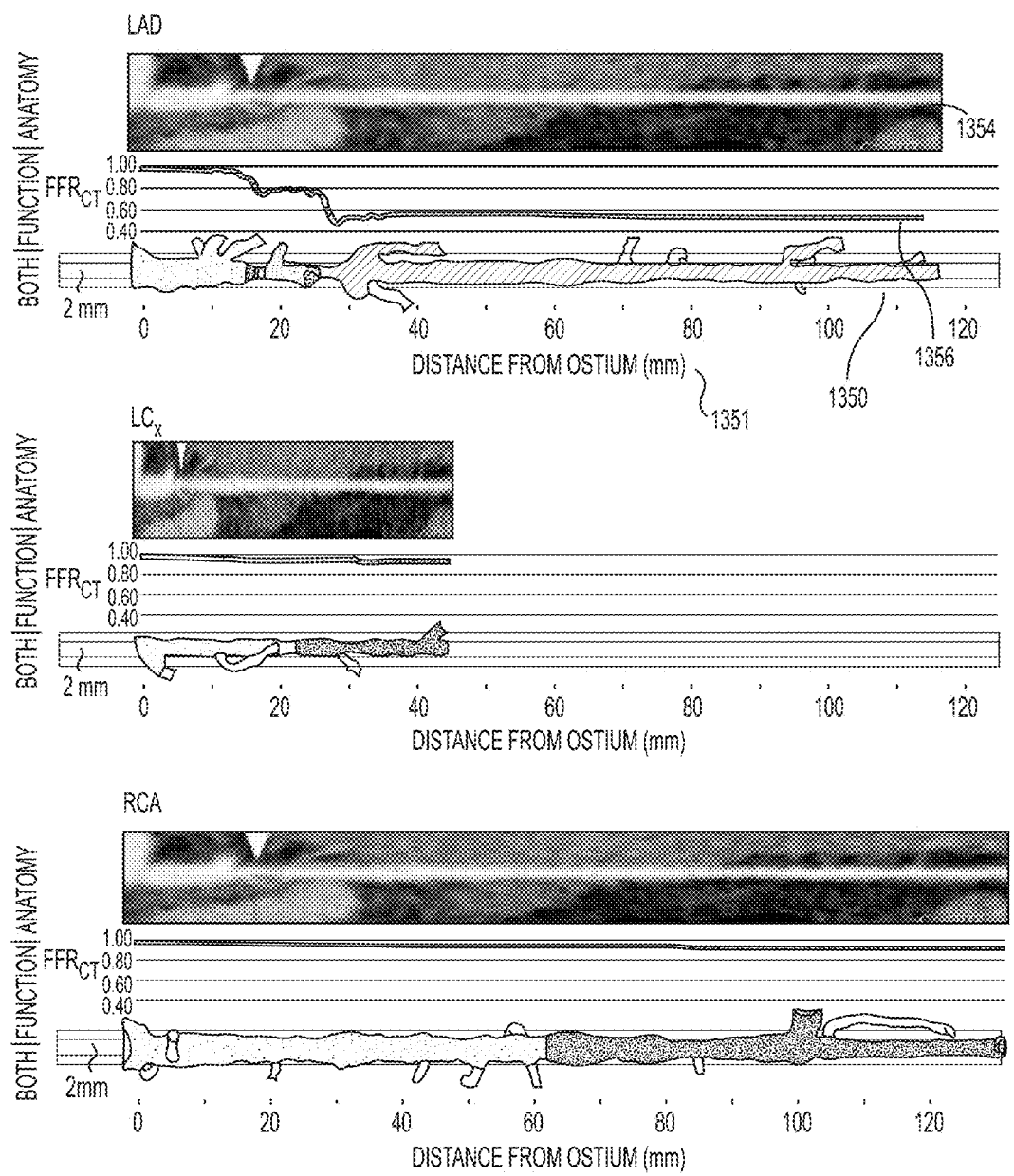

FIG. 13K illustrates a representation of one or more example arteries 1350 oriented linearly and sharing an axis 1351, the axis 1351 corresponding to an arterial characteristic, with a corresponding anatomy image 1354, which may have been used to generate the artery. An additional graph 1356, such as a pullback curve, corresponding to a second arterial characteristic, may be used to color, pattern and/or otherwise indicate the artery 1350 to create a combined representation of the arterial anatomy and representation of an arterial characteristic along the artery. For example, the anatomy image 1354 may be used to generate a representation of the artery 1350. A pullback curve 1356 representing the cFFR value along the artery may be combined with the anatomy image 1354 to form a combined artery 1350 which indicates both the anatomy of the artery and the cFFR along the artery. These steps may be repeated for other arteries and/or arterial systems.

Any of the images shown in FIGS. 13A-13K, or any image shown and/or discussed herein, may be generated using patient-specific data 10, physiological laws 20, and equations of blood flow 30. Any of the images shown and/or discussed herein may be further generated using computer 40, and may be displayed at any location in one or more medical imaging reports, an example of which is shown in FIGS. 3-6.

One or more of the steps described herein may be performed by one or more human operators (e.g., a cardiologist or other physician, the patient, an employee of the service provider providing the web-based service or other service provided by a third party, other user, etc.), or one or more computer systems used by such human operator(s), such as a desktop or portable computer, a workstation, a server, a personal digital assistant, etc. The computer system(s) may be connected via a network or other method of communicating data.

Reports may also be generated using a combination of any of the features set forth herein. More broadly, any aspect set forth in any embodiment may be used with any other embodiment set forth herein. Every device and apparatus set forth herein may be used in any suitable medical procedure, may be advanced through any suitable body lumen and body cavity, and may be used for imaging any suitable body portion.

Various modifications and variations can be made in the disclosed systems and processes without departing from the scope of the disclosure. Other embodiments will be apparent to those skilled in the art from consideration of the specification and practice of the disclosure disclosed herein. It is intended that the specification and examples be considered as exemplary only, with a true scope and spirit of the disclosure being indicated by the following claims.

What is claimed is:

1. A system for displaying a blood flow characteristic of a patient, wherein the blood flow characteristic comprises at least one of a blood flow velocity, pressure, flow rate, or fractional flow reserve (FFR), the system comprising:
at least one computer system configured to:
receive patient-specific image data regarding a geometry of the patient's heart;
create a model of blood flow through at least a portion of an artery of he patient's heart based on the patient-specific image data;
using the created model, non-invasively determine at least one value of the blood flow characteristic within the portion of the artery of the patient's heart; and
generate an electronic display comprising at least three parallel, coextensive representations of the portion of the artery and the at least one value of the blood flow characteristic, wherein indicators of the at least one value of the blood flow characteristic in at least two of the representations are aligned, and wherein:
a first representation of the at least three representations comprises a line plotted over a first axis and a second axis, wherein a first end of the first axis corresponds to a proximal end of the portion of the artery, a second end of the first axis corresponds to a distal end of the portion of the artery, and the second axis corresponds to values of the blood flow characteristic;
a second representation of the at least three representations comprises an anatomy image of the portion of the artery oriented parallel to the first axis, wherein a first end of the anatomy image corresponds to a proximal end of the portion of the artery and is aligned with the first end of the first axis, and a second end of the anatomy image corresponds to a distal end of the portion of the artery and is aligned with the second end of the first axis; and
a third representation of the at least three representations comprises a model of the portion of the artery oriented parallel to the first axis and an indicator, on the model, of the at least one value of the blood flow characteristic at a corresponding location in the portion of the artery, wherein a first end of the model corresponds to a proximal end of the portion of the artery and is aligned with the first end of the first axis and the first end of the anatomy image, and a second end of the model corresponds to a distal end of the portion of the artery and is aligned with the second end of the first axis and the second end of the anatomy image.

2. A computer-implemented method for displaying a blood flow characteristic of a patient, wherein the blood flow characteristic comprises at least one of a blood flow velocity, pressure, flow rate, or fractional flow reserve (FFR), comprising:
receiving patient-specific image data regarding a geometry of the patient's heart;
creating, using one or more microprocessors, a model of blood flow through at least a portion of an artery of the patient's heart based on the patient-specific image data;
using the created model, non-invasively determining, using the one or more microprocessors, at least one value of the blood flow characteristic within the portion of the artery of the patient's heart; and
generating, using the one or more microprocessors, an electronic display comprising at least three parallel, coextensive representations of the portion of the artery and the at least one value of the blood flow characteristic, wherein indicators of the at least one value of the blood flow characteristic in at least two of the representations are aligned, and wherein:
a first representation of the at least three representations comprises a line plotted over a first axis and a second axis, wherein a first end of the first axis corresponds to a proximal end of the portion of the artery, a second end of the first axis corresponds to a distal end of the portion of the artery, and the second axis corresponds to values of the blood flow characteristic;

a second representation of the at least three representations comprises an anatomy image of the portion of the artery oriented parallel to the first axis, wherein a first end of the anatomy image corresponds to a proximal end of the portion of the artery and is aligned with the first end of the first axis, and a second end of the anatomy image corresponds to a distal end of the portion of the artery and is aligned with the second end of the first axis; and a third representation of the at least three representations comprises a model of the portion of the artery oriented parallel to the first axis and an indicator, on the model, of the at least one value of the blood flow characteristic at a corresponding location in the portion of the artery, wherein a first end of the model corresponds to a proximal end of the portion of the artery and is aligned with the first end of the first axis and the first end of the anatomy image, and a second end of the model corresponds to a distal end of the portion of the artery and is aligned with the second end of the first axis and the second end of the anatomy image.

3. A non-transitory computer-readable medium storing instructions that, when executed by a processor, cause the processor to perform a method for displaying a blood flow characteristic of a patient, wherein the blood flow characteristic comprises at least one of a blood flow velocity, pressure, flow rate, or fractional flow reserve (FFR), the method including:

receiving patient-specific image data regarding a geometry of the patient's heart;

creating a model of blood flow through at least a portion of an artery of the patient's heart based on the patient-specific image data;

using the created model, non-invasively determining at least one value of the blood flow characteristic within the portion of the artery of the patient's heart based on the model; and generating, using the one or more microprocessors, an electronic display comprising at least three parallel, coextensive representations of the portion of the artery and the at least one value of the blood flow characteristic, wherein indicators of the at least one value of the blood flow characteristic in at least two of the representations are aligned, and wherein;

a first representation of the at least three representations comprises a line plotted over a first axis and a second axis, wherein a first end of the first axis corresponds to a proximal end of the portion of the artery, and a second end of the first axis corresponds to a distal end of the portion of the artery, and the second axis corresponds to values of the blood flow characteristic;

a second representation of the at least three representations comprises an anatomy image of the portion of the artery oriented parallel to the first axis, wherein a first end of the anatomy image corresponds to a proximal end of the portion of the artery and is aligned with the first end of the first axis, and a second end of the anatomy image corresponds to a distal end of the portion of the artery and is aligned with the second end of the first axis; and a third representation of the at least three representations comprises a model of the portion of the artery oriented parallel to the first axis and an indicator, on the model, of the at least one value of the blood flow characteristic at a corresponding location in the portion of the artery, wherein a first end of the model corresponds to a proximal end of the portion of the artery and is aligned with the first end of the first axis and the first end of the anatomy image, and a second end of the model corresponds to a distal end of the portion of the artery and is aligned with the second end of the first axis and the second end of the anatomy image.

4. The system of claim 1, wherein a color of the line at a location along the line corresponds to a value of the blood flow characteristic at a corresponding location of the portion of the artery.

5. The system of claim 1, wherein a thickness of the line at a location along the line corresponds to a lumen diameter at a corresponding location of the portion of the artery.

6. The system of claim 1, wherein the computer system is further configured to:

display a marker on the electronic display comprising the at least one value of the blood flow characteristic, wherein the marker visually indicates a point on the first representation, a first corresponding point on the second representation, and a second corresponding point on the third representation.

7. The system of claim 6, wherein the marker is displayed on the electronic display upon detecting that the at least one value of the blood flow characteristic meets a predetermined threshold.

8. The system of claim 1, wherein the model of the portion of the artery comprises a three-dimensional representation of the portion of the artery.

9. The system of claim 1, wherein the first representation further comprises one or more markers along the first axis corresponding to one or more locations of one or more arterial intersections along the portion of the artery.

10. The system of claim 1, wherein the model of the portion of the artery comprises a three-dimensional representation of the portion of the artery and corresponds to at least a portion of the model of blood flow, and wherein the first representation, the second representation, and the third representation share the first axis that corresponds to the proximal and distal ends of the portion of the artery.

11. The system of claim 1, wherein the first axis corresponds to distances of locations of the portion of the artery from the aortic ostium.

12. The method of claim 2, wherein a color of the line at a location along the line corresponds to a value of the blood flow characteristic at a corresponding location of the portion of the artery.

13. The method of claim 2, wherein a thickness of the line at a location along the line corresponds to a lumen diameter at a corresponding location of the portion of the artery.

14. The method of claim 2, further comprising:

displaying a marker on the electronic display comprising the at least one value of the blood flow characteristic, wherein the marker visually indicates a point on the first representation, a first corresponding point on the second representation, and a second corresponding point on the third representation.

15. The method of claim 14, wherein the marker is displayed on the electronic display upon detecting that the at least one value of the blood flow characteristic meets a predetermined threshold.

16. The method of claim 2, wherein the model of the portion of the artery comprises a three-dimensional representation of the portion of the artery.

17. The method of claim 2, wherein the first representation further comprises one or more markers along the first axis corresponding to one or more locations of one or more arterial intersections along the portion of the artery.

18. The method of claim 2, wherein the model of the portion of the artery comprises a three-dimensional representation of the portion of the artery and corresponds to at least a portion of the model of blood flow, and wherein the first representation, the second representation, and the third representation share the first axis that corresponds to the proximal and distal ends of the portion of the artery.

\* \* \* \* \*